United States Patent

Buck

Patent Number: 5,707,935
Date of Patent: Jan. 13, 1998

[54] HERBICIDAL COMPOUNDS

[75] Inventor: Wolfgang Buck, Ingelheim, Germany

[73] Assignee: American Cyanamid Company, Madison, N.J.

[21] Appl. No.: 699,720

[22] Filed: Aug. 6, 1996

Related U.S. Application Data

[62] Division of Ser. No. 318,327, Oct. 5, 1994, Pat. No. 5,578,550.

[30] Foreign Application Priority Data

Oct. 8, 1993 [EP] European Pat. Off. ............ 93116308

[51] Int. Cl.$^6$ .................... A01N 43/40; A01N 43/48; A01N 43/82

[52] U.S. Cl. .................... 504/253; 504/265; 514/340; 514/364

[58] Field of Search .................... 504/253, 265; 514/340, 364

[56] References Cited

U.S. PATENT DOCUMENTS 3,991,067  11/1976  Gregory et al. .................... 260/293.67
5,242,890   9/1993  Cho et al. .................... 504/100

FOREIGN PATENT DOCUMENTS 93-13083  7/1993  WIPO.

*Primary Examiner*—Allen J. Robinson
*Attorney, Agent, or Firm*—Joseph M. Mazzarese

[57] ABSTRACT

A compound of the general formula

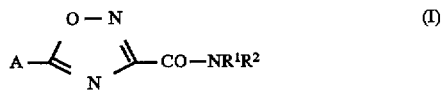

(I)

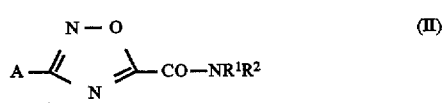

(II)

wherein A represents an optionally substituted alkyl, alkenyl, alkynyl, cycloalkyl, aryl, heteroaryl or aralkyl group, or a group of general formula X—Y—(CH$_2$)n— where X represents an optionally substituted alkyl or aryl group, n represents 1 or 2, and Y represents an oxygen atom or a group of general formula —S(O)$_m$— where m represents 0, 1 or 2; R$^1$ represents a hydrogen atom or an alkyl group; and R$^2$ represents a hydrogen atom or an optionally substituted alkyl, alkenyl, alkynyl, cycloalkyl, aryl, heteroaryl, aralkyl or heteroaralkyl group.

Also disclosed are preparative processes, and novel intermediates.

7 Claims, No Drawings

HERBICIDAL COMPOUNDS

This is a divisional of application(s) Ser. No. 08/318,327 filed on Oct. 5, 1994, now U.S. Pat. No. 5,578,550.

This invention relates to novel oxadiazole carbonamide compounds, and to their use as herbicides. The invention also relates to a process for the preparation of such compounds, and to certain novel intermediates therefor.

In accordance with the present invention there is provided a compound of the general formula

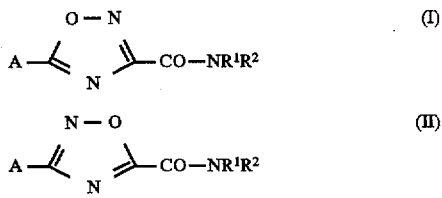

wherein A represents an optionally substituted alkyl, alkenyl, alkynyl, cycloalkyl, aryl, heteroaryl or aralkyl group, or a group of general formula X—Y—$(CH_2)_n$— where X represents an optionally substituted alkyl or aryl group, n represents 1 or 2 and Y represents an oxygen atom or a group of general formula —$S(O)_m$— where m represents 0, 1 or 2; $R^1$ represents a hydrogen atom or an alkyl group; and $R^2$ represents a hydrogen atom or an optionally substituted alkyl, alkenyl, alkynyl, cycloalkyl, aryl, heteroaryl, aralkyl or heteroaralkyl group.

Generally, when any of the above mentioned moieties comprises an alkyl group this alkyl group may be linear or branched and may suitably contain 1 to 10, preferably 1 to 6 carbon atoms. An alkenyl group may suitably contain 2 to 6 carbon atoms, preferably 2 to 4. A cycloalkyl group may have from 3 to 8 carbon atoms, most preferably 3 or, especially, 5 or 6. When any groups are designated as being optionally substituted, the substituent groups which are optionally present may be any of those customarily employed in the development of pesticidal compounds, and/or the modification of such compounds to influence their structure/activity, persistence, penetration or other property. In relation to moieties defined above as comprising an optionally substituted alkyl, alkenyl, or cycloalkyl group, including alkyl parts of aralkyl or heteroalkyl groups, specific examples of such substituents include halogen, especially fluorine, chlorine or bromine atoms, and nitro, cyano, hydroxyl, $C_{1-4}$ alkoxy, $C_{1-4}$ haloalkoxy, ($C_{1-4}$ alkoxy) carbonyl groups, amino, alkyl- and phenyl-sulphinyl, -sulphenyl and -sulphonyl groups, and $C_{1-4}$ alkylamino groups. It is preferred, however, that such moieties are unsubstituted, or halogen-substituted. In relation to moieties defined above as comprising an optionally substituted aryl or heteroaryl group, including aryl and heteroaryl parts of aralkyl and heteroaralkyl groups, optional substituents include halogen, especially fluorine, chlorine and bromine atoms, and nitro, cyano, amino, hydroxyl, $C_{1-4}$ alkyl, $C_{1-4}$ haloalkyl (especially $CF_3$) and $C_{1-4}$ alkoxy groups. 1 to 3 substituents may suitably be employed. A halogen atom may most suitably be a fluorine, chlorine or bromine atom. Suitably, A represents an optionally substituted alkyl, cycloalkyl, alkenyl, phenyl, pyridyl or thienyl group, or a group of general formula X—$S(O)_m$—$(CH_2)_n$— where X represents an optionally substituted alkyl or phenyl group, n represents 2 or, more preferably, 1, and m represents 0, 1 or, most preferably 2, or a group of general formula X—O—$(CH_2)_n$— where X represents an optionally substituted alkyl group and n represents 1 or, preferably 2. Preferably A represents an alkyl or haloalkyl group, or an alkenyl group, an optionally substituted phenyl group, or a pyridyl group or a thienyl group.

A preferred optionally substituted alkyl group A is a $C_{3-6}$ group, preferably branched.

A preferred alkenyl group A is an allyl group.

A preferred optionally substituted phenyl group A is a phenyl group which is unsubstituted, or substituted by one or two moieties independently selected from halogen atoms, especially chlorine and fluorine, and alkyl, especially $C_{1-4}$ alkyl, and haloalkyl, especially $C_{1-4}$ haloalkyl, in particular trifluoromethyl, groups. An especially preferred optionally substituted phenyl group A is unsubstituted phenyl, and phenyl mono-substituted in the 2- or 4-position, especially by chlorine, or $C_{1-4}$ alkyl.

A preferred thienyl group A is 2-thienyl. Preferred pyridyl groups A are 2-pyridyl and, especially, 3-pyridyl.

Suitably, $R^1$ represents a hydrogen atom or a $C_{1-4}$ alkyl group, for example ethyl or, especially, methyl. Preferably $R^1$ represents a hydrogen atom.

Suitably, $R^2$ represents an optionally substituted alkyl group, an alkenyl group, or an optionally substituted aryl, aralkyl or heteroaralkyl group.

Preferred optionally substituted alkyl groups $R^2$ are $C_{1-8}$ alkyl groups, unsubstituted or substituted by $C_{3-6}$ cycloalkyl, especially cyclopropyl, or by alkoxy, especially methoxy, or by propargyl.

A preferred alkenyl group $R^2$ is an allyl group.

A preferred optionally substituted aralkyl group $R^2$ is phenyl-alkylene in which the phenyl group is optionally, but preferably, substituted by 1 or 2 moieties independently selected from halogen, especially fluorine, and $C_{1-4}$ alkyl, especially methyl. The alkylene group is preferably methylene or $C_{2-4}$ alkylene, straight chained or, preferably, branched, for example —$CH(CH_3)$—. A preferred optionally substituted heteroaralkyl group $R^2$ is a furyl pyridyl or thienyl group connected to an alkylene group, the latter suitably being as defined herein with respect to aralkyl groups $R^2$. A preferred heteroaryl group thereof is 2-thienyl.

A preferred optionally substituted aryl group $R^2$ is a phenyl which is unsubstituted, or substituted by 1 or 2 moieties selected from halogen atoms and $C_{1-4}$ alkyl groups.

In general preferred groups $R^2$ conform to the general formula

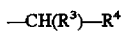

when $R^3$ represents a hydrogen atom or a $C_{1-2}$ alkyl group, and $R^4$ represents a pyridyl, furyl or thienyl group, or an optionally substituted alkyl or phenyl group. Preferably, $R^3$ represents a hydrogen atom or a methyl group, and $R^4$ represents a 2-thienyl, methyl, phenyl or 3-methylphenyl group.

Included in the scope of the present invention are (R) and (S) isomers of compounds of general formula I and II having an optical centre, and salts, N-oxides and acid addition compounds.

Particularly interesting activity appears to be found in (S)-isomer compounds of general formula I and II having the $R^2$ group —$CH(R^3)$—$R^4$, wherein the C atom is optically active.

The invention also provides a process for the preparation of a compound of general formula I or II, which comprises reacting a respective compound of the general formula III or IV

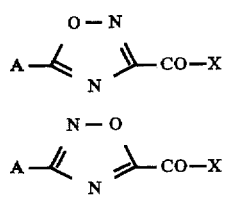

where X represents a halogen atom, especially chlorine, or a $C_{1-4}$ alkoxy group, especially methoxy or ethoxy, with a compound of general formula $HNR^1R^2$ (V).

Suitably the reaction takes place at an elevated temperature, for example 50°–100° C. Whilst an organic solvent may be employed, it is not necessary to add a solvent.

Further aspects of the invention relate to novel compounds of general formula III and IV, and to their preparation.

Ester compounds of general formula III may be prepared by treating a compound of general formula A—CO—NH—CH$_2$—CN (VI) with a compound of general formula $R^5$—ONO (VII) where $R^5$ is suitably an alkyl, for example i-propyl group, and with an alkanol X-OH. Preferably this reaction is carried out at a lowered temperature, for example −15° to 0° C., at least at the start, although the temperature may thereafter be permitted to rise, suitably to ambient temperature. An acid chloride, for example acetyl chloride, or hydrogen chloride, is suitably present.

The acetonitrile compound of general formula VI may suitably be prepared by reacting an acid chloride of general formula A—COHal (VIII) where Hal represents a halogen, especially chlorine, atom, with aminoacetonitrile hydrochloride, suitably at a temperature in the range 10°–50° C., preferably ambient temperature, and in the presence of a base. An alkali metal base, for example sodium carbonate, is suitable.

Further information applicable to each step is mentioned above for the preparation of the compounds of general formula I may be found in:

H. Brachwitz, Journal f.prakt. Chem. 314, 447 (1972)—acid chloride reaction;

H. Brachwitz, Journal f.prakt. Chem. 314, 455 (1972)—nitrite reaction;

Houben-Weyl 11/2, 20 ff, E5/2, 983 ff, Organikum, Deutscher Verlag der Wissenschaften, Berlin (1990), 409 f, (final step, amination).

Compounds of general formula IV may be prepared by reacting an oxime amide A—C(NH$_2$)=NOH (IX) with a compound of general formula HalCOCOOX (X) where Hal represents a halogen, preferably chlorine atom. Suitably the reaction takes place in the presence of an organic solvent, preferably an amine, for example pyridine. Suitably an elevated temperature, for example 50°–100° C. is employed.

Compounds of general formula IX are suitably prepared from a nitrile compound of general formula A—CN (XI), by addition of hydroxylamine hydrochloride in the presence of an alkali metal hydroxide, in the presence of water, at an elevated temperature, for example 50°–100° C.

Further information applicable to each step mentioned above for preparation of compounds of general formula II may be found in:

Freund, Lenze, Ber. 24, 2154; and S. Chiou, H. G. Shine, J. Heterocycl. Chem. 26, 125 (1989)—oxime amide preparation;

G. Palazzo, G. Strani, Gazz. Chim. Ital., 90, 1290-8 (1960); and S. Chiou, H. G. Shine, J. Heterocycl. Chem. 26, 125 (1989)—ester preparation;

Houben-Weyl 11/2, 20 ff, E5/2, 983 ff, Organikum, Deutscher Verlag der Wissenschaften, Berlin 1990, 409 f.; and DOS 2224338 (1972); C. A. 78, 72156p (1973); DOS 2140281 (1972); C. A. 77, 5486n (1972)—final step.

Acid chloride compounds of general formula III or IV may be prepared by converting an ester compound of general formula III or IV to the acid, under standard conditions using an alkali hydroxide, and converting the acid to the acid chloride under standard conditions, suitably by means of thionyl chloride.

When the target compound of general formula I is an anilide, in which $R^1$ and $R^2$ respectively represent a hydrogen atom and an optionally substituted phenyl group, a preferred method involves reacting the appropriate ester of general formula III or IV with the appropriate optionally substituted aniline in the presence of an inert solvent, for example an ether, preferably a cyclic ether, for example tetrahydrofuran, in the presence of an alkali metal base, preferably a hydride. Such a reaction is suitably effected at a temperature in the range from ambient temperature to the reflux temperature. Alternatively the method described above using an acid chloride of general formula III or IV may suitably be employed.

Further, textbook, information about the chemistry of 1,2,4-oxadiazoles can be found in Weissberger, The Chemistry of Heterocyclic Compounds, Vol. 17, 245–262 (1962); and A. R. Katritzky, C. W. Rees, Comprehensive Heterocyclic Chemistry, Pergamon Press, 1984 Vol. 6, 386–391.

The compounds of general formula I and II have been found to show interesting activity as herbicides. Accordingly, the invention further provides a herbicidal composition comprising a compound of formula I or II as defined above in association with at least one carrier, and a method of making such a composition which comprises bringing a compound of formula I or II into association with at least one carrier. Preferably there are at least two carriers, at least one of which is a surface-active agent.

The invention also provides a method of combating undesired plant growth at a locus, comprising application of such a compound or composition.

Particularly interesting activity has been found against grasses and broad leaf weeds, pre-and post-emergence. Selectivity in maize and rice has also been found. This activity provides a further aspect of the present invention.

Compounds of general formula III and IV have also been found to have some herbicidal activity and accordingly herbicidal compositions containing such compounds, and a method of combating undesired plant growth at a locus, using such a compound or composition, is also in accordance with the present invention.

In a method as mentioned above, the dosage of the active ingredient, the compound of general formula I, may, for example, be from 0.01 to 10 kg/ha, suitably 0.05 to 4 kg/ha. The locus may be an agricultural or horticultural locus, comprising, for example, a plant or soil. In a preferred method the locus contains undesired plant growth and treatment is by foliar spray application.

The invention also provides the use of a compound as defined above, as a herbicide.

A carrier in a composition according to the invention is any material with which the active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus, preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products X of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively higher concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents., 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick "mayonnaise"-like consistency.

The invention is illustrated by the following Examples. In these Examples, when an optical rotation angle is mentioned, it is the rotation in degrees caused by 1 g of the compound in 1 ml of solution, in a tube of 10 cm length, at ambient temperature, using light of the sodium D-line (589 nm).

EXAMPLE 1

5-(2-Fluorophenyl)-1,2,4-oxadiazole-3-carbonic acid
—N—(R,S)-1-phenethyl amide (Type I, A=2-F—Ph, $R^1$=H, $R^2$=Ph—CH(CH$_3$)—)

a) 2-Fluorobenzoyl-aminoacetonitrile 14.8 g Aminoacetonitrile hydrochloride was dissolved in 80 ml water. The solution was stirred while 25.37 g 2-fluorobenzoylchloride and a solution of 21.2 g sodium carbonate in 120 ml water were dropped simultaneously from two dropping funnels into it. The mixture was stirred overnight. The precipitate was filtered by suction and recrystallised from methanol plus water, filtered and dried.

Yield: 25.8 g beige solid (90.5%)
m.p. 70°–72° C.

b) 5-(2-Fluorophenyl)-1,2,4-oxadiazole-3-carbonic acid methyl ester 25.9 g Fluorobenzoyl aminoacetonitrile was dissolved in 580 ml methanol and chilled to 0°–5° C. 20.5 g Isopropyl nitrite and after that 27.5 g acetyl chloride were slowly dropped into the solution while stirring in an ice bath. The mixture was stirred over a weekend at ambient temperature. The precipitate was filtered and the solution evaporated. The precipitate and residue were together heated with water for 10 minutes to 50° C. cooled and the precipitate filtered by suction and dried. The product was recrystallised from methanol.

Yield: 21.8 g white crystals (65.4%)
m.p. 103° C.

c) 5-(2-Fluorophenyl)-1,2,4-oxadiazole-3-carbonic acid-N—(R,S)-1-phenethyl amide.

1.6 g of 5-(2-fluorophenyl)-1,2,4-oxadiazole-3-carbonic acid methyl ester and 3.5 ml R,S-1-phenylethylamine were stirred and heated to 80° C. for 3 hours. The mixture was dissolved in acetic acid ethyl ester, extracted with 2M hydrochloric acid and water, and the organic solution dried and evaporated. The residue was cleaned by chromatography (silica gel, acetic acid ethyl ester/petroleum ether 4:6 v:v)

Yield: 1.7 g white solid (75.9%)
m.p. 109° C.

The structure was confirmed by NMR: NMR 300 MHz, CDCl$_3$; 1.65 ppm D 3H; 5.4 ppm M 1H; 7.25–7.4 ppm M 8H; 7.65 ppm M 1H; 8.2 ppm T 1H.

EXAMPLE 2

5-(2-Fluorophenyl)-1,2,4-oxadiazole-3-carbonic acid —N—(S)-1-phenethyl amide

The title compound was prepared as Example 1 above, but using (S)-1-phenylethylamine instead of the racemate.

Yield: 1.59 g white solid (71.1%)
m.p. 77°–79° C.
Rotation: alpha (D,22): +21.87 in methanol
The structure was confirmed by NMR, 99% S-isomer.

EXAMPLE 3

5-t-Butyl-1,2,4-oxadiazole-3-carbonic acid-N-thiophen-2-lymethyl amide (Type I, A=t—Bu, R$^1$=H, R$^2$=2-thienyl-CH$_2$—)
a) Pivaloylaminoacetonitrile The compound was prepared according to Example 1 a) from 36.17 g pivaloylchloride and 27.76 g aminoacetonitrile hydrochloride Yield: 27.6 g white solid (65.6%)
m.p. 85° C.

b) 5-t-Butyl-1,2,4-oxadiazole-3-carbonic acid ethyl ester 9.5 g Pivaloylacetonitrile was dissolved in 150 ml ethanol. The solution was chilled to −5° C. 7.84 g Isopropylnitrite was dropped in and hydrogen chloride gas was introduced for 5 minutes. The solution was stirred for 2 hours in an ice bath and for 2 days at ambient temperature. The solution was filtered from byproduct and evaporated. The residue was cleaned by chromatography (silica gel, acetic acid ethyl ester/petroleum ether 1:1 v:v)

Yield: 11.5 g fluid
The structure was confirmed by NMR.

c) 5-t-Butyl-1,2,4-oxadiazole-3-carbonic acid-N-thiophen-2-ylmethyl amide 1.5 g 5-t-Butyl-1,2,4-oxadiazole-3-carbonic acid ethyl ester was heated with 2.5 ml 2-aminomethylthiophene (excess) to 65° C. for 6 hours. The mixture was dissolved in dichloromethane and washed with 2M hydrochloric acid and water. The solution was evaporated, the residue cleaned by chromatography and recrystallised with petroleum ether.

Yield: 1.44 g white solid (71.4%)
m.p. 83°–85° C.

The structure was confirmed by NMR:
NMR 300 MHz CDCl$_3$: 1.4 ppm S 9H; 4.8 ppm D 2H; 6.95 ppm M 1H; 7.05 ppm D 1H; 7.25 ppm M 2H.

EXAMPLE 4

3-(4-Chlorophenyl)-1.2.4-oxadiazole-5-carbonic acid n-butylamide (Type II, A=4-Cl—Ph, R$^1$=H, R$^2$=n—Bu)
a) 4-Chlorobenzyloxime amide 10.43 g Hydroxylamine hydrochloride was dissolved in 10 ml water. 6.0 g Sodium hydroxide dissolved in 25 ml water was added. This solution was mixed with 20.6 g 4-chlorobenzonitrile in 100 ml ethanol. The charge was stirred for 70 hours at 70° C. evaporated, and the residue extracted with t-butyl methyl ether. The solution was washed twice with water, dried and evaporated. The residue was cleaned by chromatography (silica gel, t-butyl methyl ether) and crystallised.

Yield: 18.15 g white solid (71%)
m.p. 130°–132° C.

b) 3-(4-Chlorophenyl)-1,2,4-oxadiazole-5-carbonic acid ethyl ester 7.6 g 4-Chlorobenzyloxime amide were dissolved in 15 ml pyridine. 6.6 g Oxalic acid monoethyl ester chloride were dropped in while chilling in an ice bath. The mixture was heated to 70° C. for 20 minutes, poured onto 100 ml ice water, stirred for 15 minutes, filtered by suction and dried.

Yield: 6.0 g white solid
m.p. 50°–52° C.
The structure was confirmed by NMR.

c) 3-(4-Chlorophenyl)-1,2,4-oxadiazole-5-carbonic acid-N-butyl amide 1.5 g 3-(4-Chlorophenyl)-1,2,4-oxadiazole-5-carbonic acid ethyl ester were stirred with 1.46 g n-butyl amine at 70° C. for 1 hour. The mixture was dissolved in 15 ml t-butyl methyl ether and washed with 2M hydrochloric acid and water. The solution was evaporated and the residue crystallised from diisopropyl ether.

Yield: 1.1 g white solid
m.p. 87° C.
The structure was confirmed by NMR:
NMR 300 MHz CDCl$_3$: 0.9 ppm T 3H; 1.4 ppm M 2H; 1.6 ppm M 2H; 3.45 ppm Q 2H; 7.1 ppm broad 1H; 7.45 ppm D 2H; 8.0 ppm D 2H.

EXAMPLE 5

3-Isopropyl-1,2,4-oxadiazole-5-carbonic acid-N-1-(thiophen-2-yl)-ethyl amide (Type II, A=i—Pr, R$^1$=H, R$^2$=2-thienyl-CH(CH$_3$)—)
a) Isobutyryl oxime amide The compound was prepared as described in Example 4 a) from 10.35 g isobutylnitrile and hydroxylamine. The reaction mixture was heated for 20 hours to 70° C. and evaporated. The residue was extracted four times with t-butyl methyl ether, and the extract was dried and evaporated.

Yield: 16.1 g colourless oil (98%) raw material, containing 82% by weight of the desired product (assessed by NMR).

b) 3-Isopropyl-1,2,4-oxadiazole-5-carbonic acid ethyl ester 10.2 g of the raw material from Example 5 a) containing 8.36 g isobutyryloxime amide was dissolved in 30 ml pyridine. 15 g Oxalic acid monoethyl ester chloride was added and the mixture heated for 15 minutes to 70° C. The mixture was poured onto 70 ml ice water, extracted with t-butyl methyl ether and the solution evaporated.

Yield: 10.4 g (68.9%) colourless fluid.

c) 3-Isopropyl-1,2,4-oxadiazole-5-carbonic acid-N-1-thiophen-2-yl)-ethyl amide 1.84 g 3-Isopropyl-1,2,4-oxadiazole-5-carbonic acid ethyl ester and 2.54 g 1-thiophen-2-ylethylamine were heated for 1 hour at 80° C. The mixture was dissolved in t-butyl methyl ether, the solution washed with 2M sulphuric acid and water and evaporated. The product was crystallised from diisopropyl ether.

Yield: 1.9 g white solid (70%)

m.p. 52°–55° C.

The structure was confirmed by NMR:

NMR 300 MHz CDCl$_3$: 1.35 ppm D 6H; 1.75 ppm D 3H; 3.1 ppm P 1H; 5.6 ppm P 1H; 7.0 ppm M 1H; 7.1 ppm D 1H; 7.2–7.3 ppm M 2H.

Anilides of general formula I or II ($R^1$=H, $R^2$=optionally substituted phenyl) were also prepared from the appropriate esters III or IV and an optionally substituted aniline in tetrahydrofuran in the presence of sodium hydride. An example is Example 6 hereunder.

EXAMPLE 6

3-Isopropenyl-1,2,4-oxadiazole-5-carbonic acid anilide (Type II, A=CH$_2$=C(CH$_3$)—, $R^1$=H, $R^2$=Ph)

5.46 g 3-Isopropene-1,2,4-oxadiazole-5-carbonic acid ethyl ester and 2.79 g aniline were dissolved in 15 ml tetrahydrofuran. A suspension of 0.79 g sodium hydride in 9 ml tetrahydrofuran was added dropwise with stirring. After addition of about half of the sodium hydride the reaction began with evolution of hydrogen. The mixture was refluxed for two hours and was stirred overnight. 100 ml Acetic acid ethyl ester and the solution was stirred with 50 ml water for a half hour. The mixture was filtered from a byproduct, the organic solution separated, dried and evaporated. The residue (2.8 g) was chromatographed over a silica column using toluene as eluant. The yield was 1.4 g of a yellow oil which was crystallised from diisopropyl ether plus petrol ether to give 0.7 g of white crystals.

m.p. 80°–82° C.

The structure was confirmed by NMR:

1H NMR 300 MHz: 2.2 ppm S 3H; 5.6 ppm S 1H; 6.2 ppm S 1H; 7.2 ppm T 1H; 7.4 ppm T 2H; 7.7 ppm T 2H; 8.75 ppm S broad 1H.

EXAMPLE 7

5-(3-Trifluoromethylphenyl)-1,2,4-oxadiazole-3-carbonic acid 3-methylanilide (Type I, A=3-CF$_3$—Ph, $R^1$=H, $R^2$=-3-CH$_3$—Ph)

3-Trifluorobenzoyl aminoacetonitrile was prepared according to Example 1a from 14.8 g aminoacetonitrile and 33.4 g 3-trifluorobenzoylchloride. Yield: 35.4g white solid (97%), m.p. 85°–87° C.

5-(3-Trifluoromethylphenyl)-1,2,4-oxadiazole-3-carbonic acid ethyl ester was prepared according to Example 1b from 35.4g 3-trifluoromethylbenzoyl aminonitrile and 17.58 g isopropylnitrite in 400 ml ethanol. Yield: 32 g white solid (72.1%), m.p. 47°–49° C.

From this ester 5-(3-trifluoromethylphenyl)-1,2,4-oxadiazole-3-carbonic acid was prepared. 32 g of the ester was dissolved in 400 ml ethanol. A solution of 5.4 g sodium hydroxide in 100 ml water was added, the mixture was stirred for 1 hour at 60° C. and cooled to ambient temperature. The precipitate was separated and the solution evaporated. Precipitate and residue were dissolved in water, the solution filtered and acidified with concentrated hydrogen chloride. The acid precipitated and was filtered by suction and dried. Yield: 17.3 g white solid (61%), m.p. 113°–114° C.

From this acid 5-(3-trifluoromethylphenyl)-1,2,4-oxadiazole-3-carbonic acid chloride was prepared. 4.6 g of the acid and 12 ml thionyl chloride were refluxed for 1.5 hours. The mixture was evaporated. Toluene was added and the mixture was again evaporated. Yield: 4.9 g oil.

2.49 g of this raw acid chloride were dissolved in 30 ml tetrahydrofuran. 1.93 g m-toluidine and 1.82 g triethylamine were added. The mixture was refluxed for 3.5 hours, filtered and the solution was evaporated. The residue was dissolved in acetic acid ester, the solution washed with water and evaporated. The residue (2.3 g) was cleaned by flash chromatography (silica column, acetic acid ester/n-hexane 6:4). The product, the title compound, was crystallised by rubbing with petrol ether.

Yield: 1.1 g (35%) white solid, m.p. 75°–78° C.

The structure was confirmed by NMR: [p ]NMR 300MHz 1H in acetone; 2.3 ppm S 3H; 7.0 ppm D 1H; 7.3 ppm T 1H; 7.7 ppm M 2H; 8.0 ppm T 1H; 8.1 ppm D 1H; 8.5 ppm M 2H; 9.9 ppm S 1H.

Further Examples of type I and II as stated above were prepared according to the methods of Examples 1 to 7 and are mentioned in Table 1 below. Structures were checked by NMR. A symbol R or S as a superscript to a carbon atom denotes the R or S isomer as being predominant.

The following further compounds set out in Table 2 below are further examples of the general formula III and IV as stated above.

TABLE 1

| Ex. No. | Compound Type | A | $R^1$ | $R^2$ | m.p. (°C.) | Rotation $[\alpha]_D^{r.t.}$ | Solvent |
|---|---|---|---|---|---|---|---|
| 8 | II | t-By | H | 2-thienyl-CH(CH$_3$)— | 85–88 | | |
| 9 | II | Ph | H | 2-thienyl-CH(CH$_3$)— | 129–139 | | |
| 10 | II | 4-Cl-Ph | H | 2-thienyl-CH(CH$_3$)— | 96–98 | | |
| 11 | II | 4-Cl-Ph | H | 2-Ph—C$^S$H(CH$_3$)— | 98–99 | +59.7° | CH$_3$OH |
| 12 | II | 4-Cl-Ph | H | 2-thienyl-CH$_2$— | 116–119 | | |
| 13 | II | i-Pr | H | n-Bu | oil | | |
| 14 | II | CH$_2$=C(CH$_3$)— | H | Ph—C$^S$H(CH$_3$)— | 168–170 | +21.5° | CH$_3$OH |
| 15 | II | CH$_2$=C(CH$_3$)— | H | n-Bu | 48–51 | | |
| 16 | II | 2,6-Cl$_2$—Ph | H | 2-thienyl-CH(CH$_3$)— | 130–132 | | |
| 17 | II | 3-pyridyl | H | 2-thienyl-CH(CH$_3$)— | 124–125 | | |
| 18 | II | 2,6-Cl$_2$—Ph | H | Ph—C$^S$H(CH$_3$)— | 119–121 | +21.0° | CH$_2$Cl$_2$ |
| 19 | II | 3-pyridyl | H | Ph—C$^S$H(CH$_3$)— | 75–95 | +60.5° | CH$_2$Cl$_2$ |
| 20 | II | 3-pyridyl | H | Et | 138–140 | | |
| 21 | II | 3-pyridyl | H | 2-thienyl-CH$_2$— | 175–177 | | |
| 22 | II | i-Pr | H | 2-thienyl-CH(C$_2$H$_5$)— | oil | | |
| 23 | II | i-Bu | H | 2-thienyl-CH(C$_2$H$_5$)— | 76–78 | | |

TABLE 1-continued

| Ex. No. | Compound Type | A | $R^1$ | $R^2$ | m.p. (°C.) | Rotation $[\alpha]_D^{r.t.}$ | Solvent |
|---|---|---|---|---|---|---|---|
| 24 | II | Ph | H | Ph—CH(CH$_3$)— | 114–115 | | |
| 25 | II | Ph | H | cyclohexyl | 109–111 | | |
| 26 | II | t-Bu | H | Ph—CH(CH$_3$)— | 112–113 | | |
| 27 | II | Ph | H | Ph—C$^R$H(CH$_3$)— | glassy | +50.3° | CH$_3$OH |
| 28 | II | Ph | H | Ph—C$^S$H(CH$_3$)— | glassy | −50.5° | CH$_3$OH |
| 29 | II | Ph | H | 2-thienyl-CH$_2$— | 115–117 | | |
| 30 | I | 4-Cl—Ph | H | Ph—CH$_2$— | 125–130 | | |
| 31 | I | 4-Cl—Ph | H | Ph—CH(CH$_3$)— | 117–120 | | |
| 32 | I | 4-Cl—Ph | H | Ph—C$^S$H(CH$_3$)— | 108–111 | +33.8° | CH$_3$OH |
| 33 | I | 4-i-Pr—Ph | H | Ph—CH$_2$— | 126–130 | | |
| 34 | I | 4-i-Pr—Ph | H | Ph—CH(CH$_3$)— | 96–100 | | |
| 35 | I | 4-i-Pr—Ph | H | Et | 84–86 | | |
| 36 | I | 2-Cl—Ph | H | Ph—CH(CH$_3$)— | 77 | | |
| 37 | I | 4-i-Pr—Ph | H | Ph—C$^S$H(CH$_3$)— | 89 | +28.3° | CH$_3$OH |
| 38 | I | t-Bu | H | Ph—CH(CH$_3$)— | 116–120 | | |
| 39 | I | 4-i-Pr—Ph | H | (3-CH$_3$—Ph)-CH$_2$— | 90 | | |
| 40 | I | Ph | H | Ph—CH(CH$_3$)— | 110–112 | | |
| 41 | I | 4-Cl—Ph | H | 2-thienyl-CH$_2$— | 150–151 | | |
| 42 | I | 4-CH$_3$—Ph | H | Ph—CH(CH$_3$)— | 120 | | |
| 43 | I | t-Bu | H | Ph—C$^S$H(CH$_3$)— | glassy | −33.7° | CH$_3$OH |
| 44 | I | Ph | H | Ph—$^S$H(CH$_3$)— | 71–72 | +32.5° | CH$_3$OH |
| 45 | I | Cl-t-Bu | H | Ph—C$^S$H(CH$_3$) | oil | −28.3° | CH$_3$OH |
| 46 | I | i-Pr | H | Ph—C$^S$H(CH$_3$)— | oil | −35.9° | CH$_3$OH |
| 47 | I | i-Pr | H | Ph—CH(CH$_3$)— | oil | | |
| 48 | I | i-Pr | H | 2-thienyl-CH$_2$— | 77–80 | | |
| 49 | I | —C(CH$_3$)(C$_2$H$_5$)$_2$ | H | Ph—CH(CH$_3$)— | oil | | |
| 50 | I | t-Bu | H | 2-thienyl-CH(CH$_3$)— | 69 | | |
| 51 | I | 2-F—Ph | H | Et | 85–87 | | |
| 52 | I | 3-CF$_3$—Ph | H | i-Pr | 72–74 | | |
| 53 | I | 3-CF$_3$—Ph | H | n-Pr | 69–73 | | |
| 54 | I | 2,4-Cl$_2$—Ph | CH$_3$ | CH$_3$ | 78–80 | | |
| 55 | I | t-Bu | H | Ph—CH$_2$ | 85–88 | | |
| 56 | I | t-Bu | H | n-Pr | oil | | |
| 57 | I | t-Bu | H | i-Pr | 76–79 | | |
| 58 | I | t-Bu | H | CH$_2$=CH—CH$_2$— | oil | | |
| 59 | I | 4-Cl—Ph | H | n-Pr | 134–135 | | |
| 60 | I | 4-Cl—Ph | H | i-Pr | 106–108 | | |
| 61 | I | 4-Cl—Ph | CH$_3$ | CH$_3$ | 91–93 | | |
| 62 | I | 3,4-Cl$_2$—Ph | H | n-Pr | 106 | | |
| 63 | I | 3,4-Cl$_2$—Ph | CH$_3$ | CH$_3$ | 98–100 | | |
| 64 | I | 4-Cl—Ph | CH$_3$ | Ph—CH$_2$— | 98 | | |
| 65 | I | 4-i-Pr—Ph | H | n-Pr | 60–61 | | |
| 66 | I | 4-i-Pr—Ph | H | CH$_2$=CH—CH$_2$— | 55 | | |
| 67 | I | 2-F—Ph | H | Ph—(CH$_2$)$_3$— | 77–78 | | |
| 68 | I | 2-Cl—Ph | H | Ph—CH$_2$— | 79–85 | | |
| 69 | I | 2-Cl—Ph | H | n-Pr | 58–59 | | |
| 70 | I | 4-i-Pr—Ph | H | Ph—C$^R$H(CH$_3$)— | 88 | −26.9° | CH$_3$OH |
| 71 | I | 2-Cl—Ph | H | 2-pyridyl-CH$_2$— | 108–112 | | |
| 72 | I | 4-CH$_3$—Ph | H | Ph—CH$_2$— | 146 | | |
| 73 | I | t-Bu | H | Ph—CH(CH$_3$)— | oil | | |
| 74 | I | 4-CH$_3$—Ph | H | Ph—C$^S$H(CH$_3$)— | 83 | +22.8° | CH$_3$OH |
| 75 | I | 2-thienyl | H | Ph—C$^S$H(CH$_3$)— | 110 | +32.8° | CH$_3$OH |
| 76 | I | 4-CH$_3$—Ph | H | 2-furyl-CH$_2$— | 136–138 | | |
| 77 | I | Ph | H | HC≡C—C(CH$_3$)$_2$— | 87–90 | | |
| 78 | I | 2-Cl—Ph | H | 3-pyridyl-CH$_2$— | 116–120 | | |
| 79 | I | 2-Cl—Ph | H | 4-pyridyl-CH$_2$ | 124–128 | | |
| 80 | I | t-Bu | H | CH$_3$O—(CH$_2$)$_3$— | oil | | |
| 81 | I | 4-i-Pr—Ph | H | cyclopropyl-CH$_2$— | 76 | | |
| 82 | I | Cl-t-Bu | H | Ph-CH(CH$_3$)— | oil | | |
| 83 | I | Cl-t-Bu | H | 2-thienyl-CH$_2$— | oil | | |
| 84 | I | i-Pr | H | Ph—CH$_2$— | 53–63 | | |
| 85 | I | t-Bu | H | cyclopropyl-CH$_2$— | 69 | | |
| 86 | I | t-Bu | H | (4-F—Ph)—CH$_2$— | 80–83 | | |
| 87 | I | t-Bu | H | 4-pyridyl-CH$_2$— | 77–81 | | |
| 88 | I | t-Bu | H | CH$_3$—(CH$_2$)$_5$—CH(CH$_3$)— | oil | | |
| 89 | I | 4-i-Pr—Ph | H | CH$_3$—(CH$_2$)$_5$—CH(CH$_3$)— | 48–51 | | |
| 90 | I | —C(CH$_3$)(C$_2$H$_5$)$_2$ | H | Ph—C$^S$H(CH$_3$)— | oil | −28.8° | CH$_3$OH |
| 91 | I | 2-Cl—Ph | H | Ph—C$^S$H(CH$_3$)— | 85–87 | +12.3° | CH$_3$OH |
| 92 | I | 2-Cl—Ph | H | 2-thienyl-C(CH$_3$)— | 100–102 | | |
| 93 | I | 2-Cl—Ph | H | 2-thienyl-CH$_2$— | 63–65 | | |
| 94 | I | 2-F—Ph | H | 2-thienyl-CH(CH$_3$)— | 170–175 | | |
| 95 | I | i-Pr | H | 2-thienyl-CH(CH$_3$)— | oil | | |
| 96 | I | —C(CH$_3$)(C$_2$H$_5$)$_2$ | H | 2-thienyl-CH(CH$_3$)— | oil | | |
| 97 | II | t-Bu | H | Ph—C$^S$H—(CH$_3$) | oil | −30.4° | CH$_3$OH |
| 98 | I | 2-F—Ph | H | 2-thienyl-CH$_2$— | 133–135 | | |
| 99 | II | i-Pr | H | Ph—C$^S$H(CH$_3$)— | oil | −32.1° | CH$_2$Cl |

TABLE 1-continued

| Ex. No. | Compound Type | A | $R^1$ | $R^2$ | m.p. (°C.) | Rotation $[\alpha]_D^{r.t.}$ | Solvent |
|---|---|---|---|---|---|---|---|
| 100 | II | $CH_2$=$C(CH_3)$— | H | 2-thienyl-$CH(CH_3)$— | 65–67 | | |
| 101 | II | $CH_2$=$C(CH_3)$— | $C_2H_5$ | $C_2H_5$ | oil | | |
| 102 | II | $CH_2$=$C(CH_3)$— | H | 2-thienyl-$CH_2$— | 57–59 | | |
| 103 | II | 2-pyridyl | H | 2-thienyl-$CH(CH_3)$— | 117–119 | | |
| 104 | I | t-Bu | H | n-octyl | oil | | |
| 105 | I | t-Bu | H | i-Bu | 92–95 | | |
| 106 | I | t-Bu | H | s-Bu | 44–46 | | |
| 107 | I | t-Bu | H | n-Bu | oil | | |
| 108 | I | t-Bu | H | 3-pyridyl-$CH_2$— | 85–88 | | |
| 109 | I | cyclopentyl | H | phenyl-$C^SH(CH_3)$— | oil | −24.3° | $CH_3OH$ |
| 110 | I | cyclopentyl | H | phenyl-$CH(CH_3)$— | 45–48 | | |
| 111 | I | t-Bu | H | 2-thienyl-$CH(C_2H_5)$— | 76 | | |
| 112 | I | cyclohexyl | H | phenyl-$CH(CH_3)$— | 40 | | |
| 113 | I | i-Bu | H | 2-thienyl-$CH(CH_3)$— | oil | | |
| 114 | I | i-Bu | H | 2-thienyl-$C^SH(CH_3)$— | oil | −27.6° | $CH_3OH$ |
| 115 | I | cyclopentyl | H | 2-thienyl-$CH(CH_3)$— | oil | | |
| 116 | I | n-Pr | H | 2-thienyl-$CH(CH_3)$— | oil | | |
| 117 | I | n-Pr | H | 2-thienyl-$C^SH(CH_3)$— | oil | −33.5° | $CH_3OH$ |
| 118 | I | 4-F—Ph | H | 2-thienyl-$CH_2$— | 106 | | |
| 119 | I | 4-F—Ph | H | 2-thienyl-$C^SH(CH_3)$— | 75–77 | +18.5° | $CH_3OH$ |
| 120 | I | i-Pr | H | 2-thienyl-$CH(CH_3)$— | 82 | | |
| 121 | II | Ph—$SO_2CH_2$ | H | 2-thienyl-$CH(CH_3)$— | 108–111 | | |
| 122 | II | 4-$CH_3$—Ph | H | 2-thienyl-$CH(CH_3)$— | 112–114 | | |
| 123 | II | 6-Cl-pyrid-2-yl | H | 2-thienyl-$CH(CH_3)$— | 147–148 | | |
| 124 | II | 4-$CH_3$—Ph | H | phenyl-$C^SH(CH_3)$— | 112–113 | +82.2° | $CH_2Cl_2$ |
| 125 | II | 6-Cl-pyrid-2-yl | H | phenyl-$C^SH(CH_3)$— | 135–138 | +73.5° | $CH_2Cl_2$ |
| 126 | I | $CH_2Cl$—$C(CH_3)2$— | H | 2-thienyl-$CH(CH_3)$— | oil | | |
| 127 | I | Ph | H | 2-thienyl-$CH(CH_3)$— | 147 | | |
| 128 | I | 4-F—Ph | H | 2-thienyl-$CH(CH_3)$— | 110 | | |
| 129 | II | Ph—CH=CH— | H | phenyl-$C^SH(CH_3)$— | 98–115 | +76.7° | $CH_2Cl_2$ |
| 130 | II | Ph—CH=CH— | H | 2-thienyl-$CH_2$— | 135–136 | | |
| 131 | II | n-Bu | H | 2-thienyl-$CH(CH_3)$— | oil | | |
| 132 | II | i-Bu | H | 2-thienyl-$CH(CH_3)$— | oil | | |
| 133 | II | i-Bu | H | 2-thienyl-$C^SH(CH_3)$— | white solid | −7.0° | $CH_2Cl$ |
| 134 | II | 4-Cl—Ph | H | 5-chloro-thien-2-yl-$CH(CH_3)$— | 127–130 | | |
| 135 | II | 4-$CF_3$—Ph | H | 2-thienyl-$CH(CH_3)$— | 90–94 | | |
| 136 | II | 4-$CH_3O$—Ph | H | 2-thienyl-$CH(CH_3)$— | 88–91 | | |
| 137 | II | 4-$CH_3O$—Ph | H | phenyl-$C^SH(CH_3)$— | oil | +58.0° | $CH_2Cl_2$ |
| 138 | II | 4-$CF_3$—Ph | H | phenyl-$C^SH(CH_3)$— | oil | +38.5° | $CH_2Cl_2$ |
| 139 | II | 4-$CF_3$—Ph | H | 2-thienyl-$CH_2$— | 102–104 | | |
| 140 | II | 4-$CF_3$—Ph | H | 2-thienyl-$CH_2$— | 122–124 | | |
| 141 | II | 4-F—Ph | H | 2-thienyl-$CH_2$— | 92–95 | | |
| 142 | I | cyclohexyl | H | 2-thienyl-$CH(CH_3)$— | 52–55 | | |
| 143 | I | cyclohexyl | H | phenyl-$C^SH(CH_3)$— | oil | −24.9°C. | $CH_3OH$ |
| 144 | II | t-Bu | H | 2-thienyl-$CH_2$— | 70–71 | | |
| 145 | II | i-Pr | H | 2-thienyl-$CH_2$— | oil | | |
| 146 | II | Ph—CH=CH— | H | 2-thienyl-$CH(CH_3)$— | 89–91 | | |
| 147 | I | 2-F—Ph | H | Ph—$C^RH(CH_3)$— | 76–77 | −22.1° | $CH_3OH$ |
| 148 | II | $CH_3$—S—$CH_2$ | H | 2-thienyl-$CH(CH_3)$— | oil | | |
| 149 | II | $CH_3$—O—$(CH_2)_2$— | H | phenyl-$C^SH(CH_3)$— | oil | Rotation angle not measured | |
| 150 | II | $CH_3$—O—$(CH_2)_2$— | H | 2-thienyl-$CH(CH_3)$— | oil | | |

TABLE 2

| Example No. | Compound Type | A | X | m.p. (°C.) |
|---|---|---|---|---|
| 151 | IV | 4-Cl—Ph | Et | 50–52 |
| 152 | IV | i-Pr | Et | oil |
| 153 | IV | 2,6-$Cl_2$—Ph | Et | 68–69 |
| 154 | IV | 3-pyridyl | Et | oil |
| 155 | IV | Ph | Et | 53–54 |
| 156 | IV | t-Bu | Et | oil |
| 157 | III | 4-i-Pr—Ph | Et | oil |
| 158 | III | 2-Cl—Ph | Et | oil |
| 159 | IV | $CH_2$=$C(CH_3)$— | Et | oil |
| 160 | IV | 2-pyridyl | Et | 85–88 |
| 161 | III | —$C(CH_3)(C_2H_5)_2$ | Et | oil |
| 162 | III | $CH_2$=CH— | Et | 49–50 |
| 163 | III | 4-F—Ph | Et | 70 |
| 164 | III | 2-Cl—Ph | Et | 55–60 |

TABLE 2-continued

| | | | | | |
|---|---|---|---|---|---|
| 165 | III | 3,4-Cl₂—Ph | Et | 94–96 | |
| 166 | III | 4-CH₃—Ph | Et | 69–70 | |
| 167 | III | 2-thienyl | Et | 69–70 | |
| 168 | IV | 4-pyridyl | Et | 87–88 | |
| 169 | IV | 4-F—Ph | Et | 49–51 | |
| 170 | IV | n-Bu | Et | oil | |
| 171 | IV | benzyl | Et | oil | |
| 172 | IV | 4-CF₃—Ph | Et | 58–61 | |
| 173 | IV | 6-Cl-pyrid-2-yl | Et | 96–99 | |
| 174 | IV | Ph—SO₂—CH₂— | Et | 136-141 | |
| 175 | IV | 4-CH₃O—Ph | Et | oil | |
| 176 | IV | 4-CH₃—Ph | Et | 57–59 | |
| 177 | III | i-Pr | Et | oil | |

| Ex. No. | Compound Type | A | R¹ | R² | m.p. (°C.) | Rotation [α]_D²² | Solvent |
|---|---|---|---|---|---|---|---|
| 178 | II | i-Pr | H | (4-t-Bu—Ph)—CH₂— | 94–97 | | |
| 179 | II | 4-Cl—Ph | H | (4-4-Bu—Ph)—CH₂— | 128–133 | | |
| 180 | II | 2-F—Ph | H | (2-thienyl)-CH(CH₃)— | 125–128 | | |
| 181 | II | 2-F—Ph | H | (2-thienyl)-CH₂— | 119–121 | | |
| 182 | II | 2-F—Ph | H | Ph—CH(CH₃)— (S) | oil | | |
| 183 | II | 2-F—Ph | H | (4-t-Bu—Ph)CH₂— | 69–77 | | |
| 184 | II | 3-F—Ph | H | (2-thienyl)-CH(CH₃)— | 116–118 | | |
| 185 | II | 3-F—Ph | H | (2-thienyl)-CH₂— | 116–118 | | |
| 186 | II | 3-F—Ph | H | Ph—CH(CH₃)— (S) | oil | | |
| 187 | II | t-Bu | H | Ph— | 91–94 | | |
| 188 | II | t-Bu | H | Tetralin-1-yl- | 128–130 | | |
| 189 | II | t-Bu | H | Tetralin-5-yl- | 185–189 | | |
| 190 | II | 4-F—Ph | H | Tetralin-1-yl- | 142–144 | | |
| 191 | II | 3-F—Ph | H | Tetralin-1-yl- | 110–111 | | |
| 192 | II | 2-F—Ph | H | Tetralin-1-yl- | 152–155 | | |
| 193 | II | t-Bu | H | (1-Naphthyl)-CH(CH₃)— (S) | glass | | |
| 194 | II | 4-F—Ph | H | (1-Naphthyl)-CH(CH₃)— | 119–122 | | |
| 195 | II | 4-F—Ph | H | (1-Naphthyl)-CH(CH₃)— (S) | 135–138 | | |
| 196 | II | 4-F—Ph | H | (3-thienyl)-CH(CH₃)— | 104–106 | | |
| 197 | II | 2,6-F₂—Ph— | H | (2-thieny)-CH₂— | 100–102 | | |
| 198 | II | t-Bu | H | (3-thienyl)-CH(CH₃)— | 81–82 | | |
| 199 | II | 2,6-F₂—Ph | H | (2-thienyl)-CH(CH₃)— | 97–99 | | |
| 200 | II | 2,6-F₂—Ph | H | Ph—CH(CH₃)— (S) | 87–91 | | |
| 201 | II | 2,4-F₂—Ph | H | (2-thienyl)-CH(CH₃)— | 102–103 | | |
| 202 | II | 2,4-F₂—Ph | H | Ph—CH(CH₃)— (S) | 44–47 | | |
| 203 | II | 4-F—Ph | H | (2-thienyl)-CH(CH₃)— (S) | 77–80 | +16.34° | CH₂Cl₂ |
| 204 | II | t-Bu | H | (2-thienyl)-CH(CH₃)— (S) | oil | +35.62° | CH₂Cl₂ |
| 205 | II | 2-F—Ph | H | 2-thienyl)-CH(CH₃)— (S) | 79–82 | +2.19° | CH₂Cl₂ |
| 206 | II | CH₃—O—(CH₂)₂ | H | (2-thienyl)-CH₂— | oil | | |
| 207 | II | 2-Cl-Pyrid-3-yl | H | (2-thienyl)-CH₂— | 97–102 | | |
| 208 | I | t-Bu | H | (1-naphthyl)-CH(CH₃)— | oil | | |
| 209 | I | 4-F—Ph | H | (3-thienyl)-CH(CH₃)— | 108–110 | | |
| 210 | I | t-Bu | H | (2-thienyl)-CH(CH₃)— (S) | oil | −53.97° | MeOH |
| 211 | I | t-Bu | H | (3-thienyl)-CH(CH₃)— | 75 | | |
| 212 | I | t-Bu | H | (1-naphthyl)-CH(CH₃)— | 89 | | |
| 213 | I | 4-F—Ph | H | (1-naphthyl)-CH(CH₃)— | 127–128 | | |
| 214 | II | 2,4-F₂—Ph | H | (3-thienyl)-CH(CH₃)— | 130–131 | | |
| 215 | I | 2-F—Ph | H | (3-thienyl)-CH(CH₃)— | | 130 | |
| 216 | I | 4-i-Pr—Ph | H | (3-thienyl)-CH(CH₃)— | | 89–91 | |
| 217 | II | 2-Cl-Pyrid-3-yl | H | (2-thienyl)-CH(CH₃)— | | 88–9 | |
| 218 | II | 2-Cl-Pyrid-3-yl | H | Ph—CH(CH₃)— | | oil | |
| 219 | II | 4-F—Ph | H | (2-thienyl)-CH(CH₃)— (S) | 59–60 | −18.63° | CH₂Cl₂ |
| 220 | I | n-Heptyl | H | (2-thienyl)-CH(CH₃)— (S) | oil | | |
| 221 | I | Cyclopentyl | H | (3-Me—Ph)—CH₃— | oil | | |
| 222 | I | 4-Cl—Ph | H | (3-thienyl)-CH(CH₃)— | 117 | | |
| 223 | I | Cyclopentyl | H | (3-thienyl)-CH(CH₃)— | oil | | |
| 224 | I | Ph | H | (3-thienyl)-CH(CH₃)— | 126 | | |
| 225 | II | i-Bu | H | (3-thienyl)-CH(CH₃)— | 68 | | |
| 226 | II | 2,6-F₂—Ph | H | (3-thienyl)-CH(CH₃)— | 137–140 | | |
| 227 | I | 4-F—Ph | H | (4-Cl—Ph)—CH(CH₃)— | 137–138 | | |
| 228 | II | 4-F—Ph | H | (4-Cl—Ph)—CH(CH₃)— | 135 | | |
| 229 | I | 2-Cl-Pyrid-3-yl | H | (2-thienyl)-CH₂— | 97–98 | | |
| 230 | I | 2-Cl-Pyrid-3-yl | H | Ph—CH(CH₃)— (S) | 110 | +9.05° | MeOH |
| 231 | I | 2-Cl-Pyrid-3-yl | H | (2-thienyl)-CH(CH₃)— | 71 | | |
| 232 | I | n-Bu | H | Ph—CH(CH₃)— | oil | −31.0 | MeOH |

TABLE 2-continued

|     |   |              | (S)                         |         |
|-----|---|--------------|-----------------------------|---------|
| 233 | I | n-Bu         | H (2-thienyl)-CH(CH$_3$)—   | oil     |
| 234 | I | n-Bu         | H (2-thienyl)-CH$_2$—       | oil     |
| 235 | I | 2-Cl-Pyrid-3-yl | H Ph—CH(CH$_3$)—         | 115–116 |
| 236 | I | Ph           | H (2-thienyl)-CH$_2$—       | 164     |

Herbicidal Activity

To evaluate their herbicidal activity, compounds of formula I, II, III and IV according to the invention were tested using a representative range of plants: maize, *Zea mays* (Z); rice, *Oryza sativa* (R); barnyard grass, *Echinochloa crus-galli* (G); oat, *Avena sativa* (O); linseed, *Linum usitatissimum* (L); mustard, *Sinapsis alba* (M); sugar beet, *Beta vulgaris* (B) and soya bean, *Glycine max* (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg and 1 kg of active material per hectare in a volume equivalent to 900 litres per hectare in the soil spray and foliar spray test, and at a dosage of level equivalent to 10 kilograms of active material per hectare in a volume equivalent to approximately 3,000 litres per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in Table 3 below. A blank space in Table 3 for a compound for which other results are given indicates a rating 0. Where a compound has no results and entirely blank spaces, this indicates that data is not yet available, for this compound. An asterisk denotes that a test was not undertaken, or was not completed.

TABLE 3

| | Soil drench 10 Kg/ha | | | | | | | Dosage | Foliar Spray | | | | | | | | Pre-emergence | | | | | | | |
|---|---|---|---|---|---|---|---|---|---|---|---|---|---|---|---|---|---|---|---|---|---|---|---|---|
| Ex. No. | Z | R | G | O | L | M | B | S | kg/ha | Z | R | G | O | L | M | B | S | Z | R | G | O | L | M | B | S |
| 1 | | | 6 | 5 | 4 | 6 | 8 | | 5 | 3 | | 9 | 6 | 7 | 9 | 9 | 7 | | | | | | | | |
| | | | | | | | | | 1 | | | 9 | 3 | 6 | 7 | 9 | 6 | | | | | | | | |
| 2 | | | 5 | | 2 | 7 | 3 | 5 | 5 | 4 | | 9 | 5 | 8 | 8 | 9 | 7 | | | 4 | | | 3 | 5 | 3 |
| | | | | | | | | | 1 | 2 | | 8 | 2 | 8 | 7 | 9 | 7 | | | | | | | 2 | |
| 3 | 4 | 4 | 6 | 4 | 7 | 6 | 4 | 6 | 5 | 4 | 4 | 9 | 4 | 8 | 8 | 9 | 9 | 2 | | 9 | 4 | 3 | 9 | 9 | 3 |
| | | | | | | | | | 1 | 2 | 3 | 9 | 3 | 2 | 7 | 8 | 2 | | | 2 | 2 | | 2 | 2 | |
| 4 | | | | | | | | | 5 | 2 | | 4 | 1 | 7 | 9 | 9 | 4 | | | | | | 6 | 1 | |
| | | | | | | | | | 1 | | | | | 6 | 8 | 8 | 3 | | | | | | 2 | | |
| 5 | 7 | | 9 | 8 | 9 | 9 | 9 | 8 | 5 | 2 | | 9 | 7 | 9 | 9 | 9 | 8 | 4 | | 8 | 7 | 7 | 8 | 8 | 5 |
| | | | | | | | | | 1 | | | 9 | 5 | 8 | 9 | 9 | 7 | 1 | | 8 | 5 | 7 | 8 | 8 | 2 |
| 7 | | | | | | | | | 5 | 2 | | 3 | | 1 | 6 | 4 | 2 | | | | | | | | |
| | | | | | | | | | 1 | | | | | | | 2 | | | | | | | | | |
| 8 | 7 | 2 | 9 | 8 | 9 | 9 | 9 | 8 | 5 | 2 | 4 | 9 | 7 | 9 | 9 | 9 | 8 | 4 | 5 | 8 | 7 | 6 | 9 | 8 | 2 |
| | | | | | | | | | 1 | | 2 | 9 | 7 | 8 | 9 | 9 | 8 | 2 | 3 | 7 | 6 | 6 | 8 | 8 | |
| 9 | | | | | 5 | 6 | 9 | | 5 | | | 9 | 5 | 8 | 8 | 9 | 6 | | | | | | | | |
| | | | | | | | | | 1 | | | 8 | 4 | 7 | 7 | 9 | 5 | | | | | | | | |
| 10 | | | | | | | | | 5 | 5 | | 8 | 6 | 9 | 8 | 9 | 7 | | | | | | 4 | 2 | |
| | | | | | | | | | 1 | 2 | | 8 | 5 | 8 | 8 | 9 | 7 | | | | | | | | |
| 11 | | | | | | | | | 5 | 6 | | 9 | 6 | 8 | 9 | 9 | 7 | | | | | | 4 | 4 | |
| | | | | | | | | | 1 | | | 8 | 5 | 8 | 8 | 9 | 7 | | | | | | 2 | 2 | |
| 12 | | | | | | | | | 5 | 4 | | 8 | 7 | 9 | 8 | 9 | 6 | | | | | | 5 | 2 | 1 |
| | | | | | | | | | 1 | 2 | | 8 | 5 | 8 | 8 | 9 | 5 | | | | | | 4 | | |
| 13 | | | 5 | 4 | 3 | 7 | 6 | 5 | 5 | | | 7 | 1 | 6 | 7 | 2 | 4 | | | 6 | 2 | | 4 | 2 | |
| | | | | | | | | | 1 | | | 2 | | 2 | | | 2 | | | 4 | | | 2 | | |
| 14 | 4 | | 5 | | 6 | 8 | 4 | 8 | 5 | 2 | | 8 | 6 | 7 | 9 | 9 | 6 | | | | | | | | |
| | | | | | | | | | 1 | | | 7 | 2 | 5 | 5 | 4 | 5 | | | | | | | | |
| 15 | | | | | | | | | 5 | | | 6 | | 2 | 6 | 4 | | | | | | | | | |
| | | | | | | | | | 1 | | | 2 | | | 5 | 2 | | | | | | | | | |
| 16 | 2 | | | 6 | | 5 | 6 | | 5 | | | 7 | | 7 | 9 | 9 | 2 | | | 4 | | 4 | 5 | 6 | 4 |
| | | | | | | | | | 1 | | | 6 | | 6 | 8 | 8 | | | | 4 | | | 2 | 2 | 2 |
| 17 | | | 4 | | 7 | 5 | 6 | | 5 | 2 | | 9 | 6 | 9 | 9 | 9 | 6 | | | 7 | | | 4 | 5 | |

TABLE 3-continued

| | | | | | | | | | | | | | | | | | | | | | | | |
|---|---|---|---|---|---|---|---|---|---|---|---|---|---|---|---|---|---|---|---|---|---|---|---|
| 18 | | | | | | | | | 1 5 1 | 2 | 8 8 7 | | 7 8 6 | 8 8 8 | 7 9 7 | 2 4 | | 2 | | 2 2 | 2 7 5 | |
| 19 | | | 4 | | 5 | 6 | 6 | | 5 1 | 4 | 8 7 | 2 5 | 7 6 | 8 7 | 9 | 2 | | | | | | |
| 20 | | | | | | | | | 5 1 | | 2 | | | 2 2 | 5 | | | | | | | |
| 21 | | | | | | | | | 5 1 | | 2 | | | 7 6 | 5 2 | | | | | | | |
| 22 | | | | | 5 | 6 | 8 | | 5 1 | 4 | 8 6 | | 7 5 | 9 7 | 8 7 | 4 2 | | 6 | | 7 2 | 6 5 | |
| 23 | | | | | 5 | 7 | | | 5 1 | | 8 7 | 4 | 7 6 | 8 7 | 9 8 | 6 | | 6 2 | 2 | 7 2 | 6 5 | |
| 24 | | | | | 7 | 6 | 2 | | 5 1 | | 7 6 | 8 7 | 8 7 | 8 8 | 9 5 | 6 | | | | | | |
| 25 | | | | | | | | | 5 1 | | | | 4 2 | 7 | | | | | | | | |
| 26 | 7 | 4 | 8 | 7 | 9 | 9 | 9 | 7 | 5 1 | | 7 5 | 4 2 | 7 6 | 9 8 | 9 8 | 5 4 | | 2 | | 6 5 | 7 5 | |
| 27 | | | | | | 6 | 2 | | 5 1 | 2 | 8 7 | 6 2 | 5 4 | 7 7 | 9 8 | 2 | | 7 2 | | 8 5 | 5 2 | 4 2 |
| 28 | | | | | | | | | 5 1 | 4 2 | 9 8 | 5 2 | 8 7 | 8 6 | 8 8 | 6 5 | 2 | 7 6 | | 7 5 | 7 4 | |
| 29 | | | 4 | | 5 | 6 | 5 | | 5 1 | 2 2 | 8 2 | 4 2 | 5 2 | 4 8 | 8 2 | 4 | | | | 6 4 | 2 | |
| 30 | | | | | | | | | 5 1 | 2 | 4 | 2 | 7 5 | 9 9 | 9 9 | 4 4 | | | | | | |
| 31 | | | | | | | | | 5 1 | | 9 8 | 4 2 | 8 7 | 9 8 | 9 9 | 7 6 | | | | | | |
| 32 | | | | | | 4 | 2 | | 5 1 | 2 | 8 7 | 4 2 | 9 6 | 7 7 | 9 9 | 6 4 | | | | | | |
| 33 | | | | | | | | | 5 1 | | 6 2 | 4 | 8 7 | 7 | 9 9 | | | | | | | |
| 34 | | | | | | | | | 5 1 | 4 | 9 8 | 4 2 | 9 8 | 8 7 | 9 9 | 4 2 | | 5 | | 6 2 | 4 | 5 |
| 35 | | | | | | | | | 5 1 | | 8 2 | | 7 6 | 6 9 | 9 | | | | | 4 2 | 3 | |
| 36 | | | | | | | | | 5 1 | 2 | 7 6 | 4 | 9 7 | 8 8 | 9 9 | 4 2 | | | | | | |
| 37 | | | | | | | | | 5 1 | 5 2 | 4 1 | 9 8 | 4 2 | 9 7 | 7 7 | 9 9 7 5 | | | | | | |
| 38 | 4 | | | 6 | 2 | 5 | 6 | 5 | 5 1 | 3 | 9 7 | 4 2 | 8 5 | 9 8 | 9 9 7 | 8 | 6 5 | 4 | 8 7 | 7 6 | 8 | 9 9 | 9 9 | 6 5 |
| 39 | | | | | | | | | 5 1 | | 4 | | 6 5 | 9 7 | 9 9 | 4 2 | | | | | | |
| 40 | | | | | | 2 | 4 | 3 | 5 1 | 4 2 | 3 1 | 9 8 | 4 2 | 8 6 | 9 8 | 9 9 | 7 6 | | | 4 | 1 | 7 4 | 7 2 | 2 |
| 41 | | | | | | | | | 5 1 | | 4 2 | 2 6 | 8 | 2 6 | 8 7 | 9 9 | 9 5 | 6 | | | 6 2 | 2 |
| 42 | | | | | | | | | 5 1 | | 3 | 2 | 9 8 | 4 2 | 9 8 | 8 8 | 8 5 | 6 | | | 6 5 | 6 2 | 3 |
| 43 | 7 | 9 | 8 | 8 | 9 | 9 | 9 | 8 | 5 1 | 4 2 | 8 8 | 9 9 | 8 6 | 9 7 | 9 8 | 9 9 | 9 7 | 7 2 5 | 9 7 | 7 4 | 8 6 | 9 9 | 9 8 | 6 5 |
| 44 | 7 | 6 | 7 | 8 | 9 | 9 | 7 | 5 | 5 1 | | 9 8 | 4 2 | 9 7 | 7 6 | 9 9 | 8 6 | | 6 2 | | 2 | 9 7 | 2 | |
| 45 | 7 | 8 | 8 | 8 | 8 | 9 | 9 | 8 | 5 1 | 4 2 | 1 | 9 8 | 7 4 | 8 2 | 9 8 | 9 9 | 7 6 | 7 | 7 | | | | |
| 46 | 7 | 8 | 9 | 8 | 8 | 9 | 9 | 8 | 5 1 | 6 2 | 4 | 9 9 | 7 2 | 8 4 | 9 6 | 9 9 | 8 6 | 6 | 8 4 | 6 | | 4 | 6 | |
| 47 | 7 | 8 | 9 | 7 | 9 | 9 | 8 | 8 | 5 1 | 7 5 | 4 2 | 9 8 | 8 5 | 8 7 | 8 8 | 9 5 | 7 | 5 | 7 5 | | 6 2 | 7 4 | 8 2 | 4 2 |
| 48 | 7 | 5 | 9 | 6 | 8 | 9 | 9 | 8 | 5 1 | 2 | 9 8 | 4 2 | 7 2 | 9 8 | 9 8 | 7 6 | 5 | 2 | 8 8 | 6 5 | 7 6 | 9 7 | 7 6 | 2 |
| 49 | 6 | | 5 | | | 8 | 9 | | 5 1 | | | | 9 8 | 6 2 | 7 5 | 8 7 | 9 9 | 4 2 | | 2 | | 7 2 | 2 1 | |
| 50 | 8 | 5 | 9 | 8 | 7 | 8 | 9 | 8 | 5 1 | 6 2 | | 9 9 | 7 5 | 9 8 | 9 9 | 9 9 | 8 7 | 4 | | 9 7 | 6 5 | 7 | 8 8 | 9 8 | 4 2 |
| 51 | | | | | * | 3 | 4 | 1 | 5 1 | | 4 1 | 6 4 | 2 2 | 6 6 | 8 6 | 7 5 | | | | | 2 | 5 1 | 3 | |
| 52 | | | | | | | | | 5 1 | 2 | 1 | 4 2 | | 3 2 | 3 1 | | | | | | | | |
| 53 | | | | | | | | | 5 1 | 2 | | 5 2 | 1 | 2 3 | 5 3 | 3 1 | | | | | | | |
| 54 | | | | | | | | | 5 1 | | 2 | 6 2 | 2 | 6 3 | 8 4 | 8 2 | 4 1 | | | | | | |
| 55 | | | | | 4 | 8 | 6 | 4 | 5 1 | | 2 2 | 6 3 | 3 | 6 7 | 9 4 | 9 2 | 5 | | 6 5 | | 2 | 7 2 | 7 | |
| 56 | | | | | 2 | 3 | 5 | 4 | 5 1 | | 2 | | 2 | 6 5 | 5 3 | 4 2 | | | 6 | | 3 | 3 | 3 | |

TABLE 3-continued

| | | | | | | | | | | | | | | | | | | | | | | | |
|---|---|---|---|---|---|---|---|---|---|---|---|---|---|---|---|---|---|---|---|---|---|---|---|
| 57 | | | | 4 | 2 | 3 | 51 | | | | | 5 2 | 6 2 | 4 2 | 3 1 | | | | | | | | |
| 58 | | | 4 | 4 | 4 | * | 51 | | | | | 4 | 7 3 | 5 | 5 3 | | | | | | | | |
| 59 | | | | | | | 51 | | | | | 6 2 | 9 8 | 8 4 | 3 | | | | | | | | |
| 60 | | | 4 | 7 | 2 | | 51 | | | 3 | 2 | 6 4 | 9 7 | 7 5 | 2 | | | | | | 6 | 5 | |
| 61 | | | | | | | 51 | 4 | 2 | 6 2 | 3 | 5 2 | 7 6 | 7 2 | 6 | * | * | * | * | * | * | * | * |
| 62 | | | | | | | 51 | 3 | | 4 1 | | 5 4 | 8 6 | 3 | 4 | | | | | | | | |
| 63 | | | | | | | 51 | 4 1 | 3 | 4 | 3 | 4 2 | 7 5 | 4 | 4 3 | | | | | | | | |
| 64 | | | | | | | 51 | | | 7 6 | | 6 4 | 9 8 | 7 7 | | | | | | | | | | |
| 65 | | | | | | | 51 | 4 | | 6 2 | | 7 6 | 6 6 | 8 7 | | | | | | | 3 | 2 | |
| 66 | | | | 5 | | | 51 | 3 | | 6 2 | 3 | 7 5 | 7 7 | 9 7 | | | | | | | 7 2 | 3 | |
| 67 | | | | | | | 51 | 3 | | | | 2 | 4 | 3 | | | | | | | | | |
| 68 | | | | | | | 51 | 4 2 | | 7 5 | 4 | 8 5 | 9 7 | 3 8 | | | | | | | 2 | 3 | |
| 69 | | | | | | | 51 | | | 4 2 | 2 | 5 2 | 7 4 | 6 2 | 5 2 | | | | | | 3 | | |
| 70 | | | | | | | 51 | 2 | | 7 2 | | 4 2 | 9 5 | 8 4 | 3 2 | | | | | | | | |
| 71 | | | | | | | 51 | 4 | | 2 | | 6 5 | 4 2 | 3 | | | | | | | | | |
| 72 | | | | | | | 51 | | | | | 4 2 | 6 5 | | | | | | | | 4 2 | 3 | |
| 73 | 4 | | 2 | 7 | 8 | 5 | 51 | | | 9 2 | 2 | 5 4 | 6 2 | 7 2 | 5 2 | | 2 | 5 2 | | | 7 2 | 5 2 | |
| 74 | | | | 7 | 7 | 5 | 51 | | | | | 8 5 | 8 8 | 9 4 | 5 | | | | | | | | |
| 75 | 4 | 3 | 5 | 4 | 8 | 6 | 51 | | | 8 6 | | 7 5 | 8 7 | 9 8 | 5 4 | | | | | | | | |
| 76 | | | | | | | 51 | | | | | 5 1 | 1 | | | | | | | | | | |
| 77 | | | 3 | 8 | 7 | | 51 | | | 9 2 | 1 | 6 2 | 9 4 | 8 2 | 6 4 | | | | | | 4 2 | | 2 |
| 78 | | | | | | | 51 | | | 4 | | 5 | 7 | 1 | 2 | | | | | | | | |
| 79 | | | | | | | 51 | 1 | | 7 2 | 3 | 7 5 | 8 7 | 9 8 | 5 | | | | | | | | |
| 80 | | | 2 | 1 | 2 | 4 | 51 | | | 3 2 | 1 | 4 2 | 4 | 2 3 | 4 | | | | | | | | |
| 81 | | | | | | | 51 | 1 | | 3 6 | | 8 7 | 8 7 | 8 | 2 | | | | | | | | |
| 82 | 6 | 2 | 7 | 7 | 6 9 | 8 | 5 51 | 4 | | 9 4 | 5 | 7 2 | 8 7 | 9 8 | 8 2 | | 2 | | | | 5 | 8 | |
| 83 | 6 | | 5 | 4 | 8 | 8 | 7 51 | | | 9 7 | 2 | 6 2 | 9 8 | 8 8 | 8 4 | | | | | | 6 2 | | |
| 84 | 4 | | 7 | | 4 7 | 6 | 5 51 | | | 9 2 | 2 | 4 4 | 8 2 | 9 2 | 6 | | | | | | | | |
| 85 | 4 | | 5 | 6 | 7 6 | 5 | 5 51 | 4 | 1 | 4 2 | | 5 | 6 2 | 5 | | | 4 2 | | | | 2 | 1 | 4 |
| 86 | 4 | | 5 | 6 | 7 8 | 8 | 5 51 | | | 6 2 | 4 2 | 7 5 | 8 7 | 9 7 | 6 5 | 2 | 4 2 | | | | 5 2 | 6 2 | 2 |
| 87 | | | 4 | 3 | 4 7 | 3 | 51 | | 2 | 7 | 2 | 4 3 | 6 4 | 7 4 | 3 | | 3 | 1 | | | 4 | 1 | |
| 88 | | | | 2 | 2 | 4 | 51 | 2 | | 7 4 | | | 2 | 4 | 2 | | | | | | | | |
| 89 | | | | | | | 51 | 1 1 | | 3 2 | | 1 | 4 1 | | | | | | | | | | |
| 90 | 5 | 4 | 8 | 5 | 2 9 | 9 | 5 51 | 4 2 | | 9 8 | 4 2 | 8 5 | 9 8 | 9 8 | 7 5 | 2 | 4 2 | 4 3 | | | 6 5 | 4 2 | |
| 91 | 2 | | 5 | | 5 | 6 | 51 | 4 | | 9 8 | 7 4 | 8 7 | 8 8 | 8 8 | 7 7 | | 3 | | 2 | | 3 5 | 4 | 2 |
| 92 | | | | | | | 51 | | | 8 8 | 6 5 | 7 6 | 8 7 | 9 8 | 6 5 | | | | | | | | |
| 93 | | | | | | | 51 | 2 | | 9 8 | 6 2 | 7 5 | 7 7 | 9 8 | 2 | | | | | | | | |
| 94 | | 2 | | 6 | 8 | 8 | 4 51 | 4 | | 9 8 | 4 2 | 9 8 | 8 8 | 9 8 | 6 5 | | | | | | | | |
| 95 | 7 | * | 8 | 7 | 8 | 8 8 | 7 51 | 2 | | 9 9 | 4 2 | 8 5 | 9 9 | 8 6 | | 2 | 9 8 | 7 2 | 7 6 | 8 8 | 8 7 | 2 | |
| 96 | 5 | | 7 | 4 | 8 | 8 5 | 4 51 | 2 | | 9 | 7 | 9 | 8 | 9 | 6 | | 7 | | 2 | 7 | 7 | | |

TABLE 3-continued

| | | | | | | | | | | | | | | | | | | | | | | | | |
|---|---|---|---|---|---|---|---|---|---|---|---|---|---|---|---|---|---|---|---|---|---|---|---|---|
| 97 | 4 | 1 | 6 | 7 | 7 | 7 | 8 | 7 | 1 | | | 8 | 2 | 8 | 8 | 8 | 2 | | | 7 | | | 2 | 5 |
| | | | | | | | | | 5 | | 3 | 8 | 3 | 7 | 9 | 9 | 7 | 2 | 2 | 6 | 2 | 3 | 8 | 8 | 2 |
| 98 | | | 4 | | 7 | 6 | | | 1 | | | 7 | 2 | 6 | 9 | 9 | 3 | | | 2 | | | 4 | 6 | |
| | | | | | | | | | 5 | | | 9 | 6 | 9 | 8 | 9 | | | | 4 | 2 | 4 | 5 | 4 | |
| 99 | 5 | | 7 | | 5 | 7 | 5 | 7 | 1 | | | 8 | | 8 | 8 | 8 | | | | 2 | | | | 4 | |
| | | | | | | | | | 5 | 5 | 2 | 9 | 7 | 6 | 9 | 9 | 6 | 2 | | 8 | 2 | 5 | 9 | 8 | |
| 100 | | | 7 | | 6 | 5 | 7 | 4 | 1 | | | 8 | 5 | 5 | 8 | 8 | 2 | | | 7 | | 2 | 7 | 7 | |
| | | | | | | | | | 5 | | | 9 | 7 | 8 | 8 | 9 | 6 | | | 9 | | 6 | 7 | 2 | |
| 101 | | | | | | 4 | | | 1 | | | 8 | 5 | 6 | 7 | 9 | 5 | | | 7 | | | 5 | | |
| | | | | | | | | | 5 | | | 7 | 2 | | 6 | 5 | 2 | | | | | | | | |
| 102 | | | | | 3 | 5 | | | 1 | | | 5 | | | 2 | 2 | | | | | | | | | |
| | | | | | | | | | 5 | | | 9 | 6 | 5 | 9 | 9 | 4 | | | 6 | | | 2 | | |
| 103 | | | 7 | 4 | 9 | 8 | | 2 | 1 | | | 8 | | 2 | 8 | 7 | 2 | | | 5 | | | | | |
| | | | | | | | | | 5 | | | 8 | 6 | 8 | 4 | 9 | 2 | | | 7 | 6 | 2 | 9 | 7 | |
| 104 | | | | | | | | | 1 | | | 7 | 2 | 5 | 2 | 9 | | | | | 2 | | | | |
| | | | | | | | | | 5 | | | 2 | | | 4 | 5 | 4 | | | | | | | | |
| 105 | 2 | | 4 | | 2 | 5 | 4 | 4 | 1 | | | | | | 2 | 2 | 2 | | | | | | | | |
| | | | | | | | | | 5 | | | | | | 5 | 4 | 4 | | | | | | | | |
| 106 | 2 | | 5 | 4 | 3 | 6 | 5 | 4 | 1 | | | | | | 2 | 2 | 2 | | | | | | | | |
| | | | | | | | | | 5 | | | 6 | | 4 | 7 | 4 | 5 | | | 4 | | 2 | 4 | 5 | 6 |
| 107 | 4 | | 5 | 2 | 7 | 8 | 6 | 5 | 1 | | | | | | 5 | 2 | | | | | | | 2 | 2 | 2 |
| | | | | | | | | | 5 | | | 5 | | 4 | 8 | 6 | 5 | 2 | | 7 | 2 | | 6 | 2 | 4 |
| 108 | | | | | | 4 | 1 | 1 | 1 | | | 2 | | 2 | 7 | 2 | 2 | | | 5 | | | 5 | | 2 |
| | | | | | | | | | 5 | | | 3 | 2 | | 6 | 6 | 3 | | | | | | 1 | | |
| 109 | * | * | * | * | * | * | * | * | 1 | | | | | | 2 | 4 | | | | | | | | | |
| | | | | | | | | | 5 | 4 | 5 | 9 | 6 | 6 | 8 | 9 | 8 | 2 | | 7 | | | 6 | 8 | 2 |
| 110 | 7 | 6 | 8 | 6 | 9 | 9 | 9 | 7 | 1 | 2 | 2 | 8 | 2 | 4 | 8 | 9 | 6 | | | 2 | | | 6 | 2 | |
| | | | | | | | | | 5 | 2 | | 9 | 2 | 6 | 8 | 9 | 6 | | | | | | | | |
| 111 | * | * | * | * | * | * | * | * | 1 | | | 4 | | 2 | 8 | 8 | 5 | | | | | | | | |
| | | | | | | | | | 5 | 2 | 3 | 9 | 4 | 7 | 9 | 8 | 6 | | | 9 | 6 | 5 | 1 | 4 | |
| 112 | 4 | | 5 | 6 | 7 | 9 | 7 | 6 | 1 | | 3 | 6 | 1 | 4 | 8 | 7 | 4 | | | 2 | 2 | | | 2 | |
| | | | | | | | | | 5 | 3 | 7 | 9 | 4 | 8 | 9 | 7 | 7 | | | | | 2 | | 5 | |
| 113 | 5 | | 8 | 8 | 5 | 9 | 9 | 8 | 1 | | 2 | 7 | | 6 | 8 | 7 | 4 | | | | | | | 2 | |
| | | | | | | | | | 5 | 4 | | 9 | 6 | 8 | 9 | 9 | 8 | 6 | | 8 | 5 | 6 | 9 | 9 | 4 |
| 114 | 7 | | 7 | | 6 | 7 | 8 | 9 | 1 | 2 | | 9 | 5 | 7 | 9 | 9 | 7 | | | 4 | 2 | | 8 | 5 | |
| | | | | | | | | | 5 | 4 | | 9 | 6 | 8 | 9 | 9 | 7 | 6 | | 8 | | 4 | 9 | 9 | |
| 115 | 6 | | 8 | | 7 | 9 | 9 | 8 | 1 | | | 8 | 5 | 8 | 9 | 6 | | | | 2 | | | 6 | 2 | |
| | | | | | | | | | 5 | 2 | | 9 | 6 | 9 | 9 | 9 | 9 | | | 7 | 3 | 2 | 9 | 8 | 2 |
| 116 | 7 | | 8 | 9 | 9 | 9 | 9 | 8 | 1 | | | 9 | 2 | 6 | 8 | 9 | 8 | | | 2 | | | 8 | 6 | |
| | | | | | | | | | 5 | 5 | | 9 | 7 | 7 | 8 | 8 | 8 | 4 | | 9 | 2 | 5 | 8 | 8 | 2 |
| 117 | 7 | 7 | 8 | 7 | 7 | 9 | 9 | 8 | 1 | 2 | | 8 | 2 | 5 | 7 | 8 | 4 | | | 6 | | | 2 | 4 | |
| | | | | | | | | | 5 | 5 | | 7 | 6 | 5 | 8 | 9 | 8 | 5 | 3 | 8 | 5 | 7 | 8 | 7 | 6 |
| 118 | | | | | 4 | 6 | 9 | 4 | 1 | 2 | | 5 | 2 | 2 | 7 | 6 | 4 | 2 | | 6 | 2 | | 5 | 4 | 2 |
| | | | | | | | | | 5 | 2 | 5 | 7 | 5 | 9 | 9 | 9 | 8 | | | | | | | | |
| 119 | | | 8 | 7 | 7 | 6 | 9 | 6 | 1 | | 4 | 5 | 4 | 6 | 9 | 9 | 6 | | | | | | | | |
| | | | | | | | | | 5 | 3 | 4 | 9 | 4 | 8 | 9 | 9 | 8 | | | 1 | 1 | | 7 | 9 | 3 |
| 120 | | | | | 3 | | 2 | 1 | 1 | 3 | 4 | 9 | 4 | 7 | 9 | 9 | 8 | | | | | | | 4 | |
| | | | | | | | | | 5 | 5 | 5 | 9 | 6 | 9 | 8 | 9 | 7 | | | | | | | | |
| 121 | | | | | 6 | 9 | 5 | 7 | 1 | 4 | 3 | 5 | 3 | 5 | 8 | 9 | 6 | | | | | | | | |
| | | | | | | | | | 5 | | 2 | 8 | 2 | 8 | 9 | 9 | 8 | | | | | | 6 | | |
| 122 | | | | | | 5 | 6 | | 1 | | | 6 | | 7 | 9 | 9 | 6 | | | | | | 4 | | |
| | | | | | | | | | 5 | | | 9 | 7 | 8 | 9 | 9 | 8 | | | | | | | | |
| 123 | | | 3 | 8 | 5 | 7 | 9 | 5 | 1 | | | 8 | 6 | 7 | 9 | 9 | 7 | | | | | | | | |
| | | | | | | | | | 5 | | | 9 | 8 | 8 | 9 | 9 | 8 | | | | | | | | |
| 124 | | | | | | 6 | 4 | | 1 | | | 9 | 7 | 7 | 9 | 9 | 7 | | | | | | | | |
| | | | | | | | | | 5 | 6 | 5 | 9 | 7 | 8 | 9 | 9 | 7 | | | | | | | | |
| 125 | 7 | 8 | 9 | 9 | 7 | 9 | 9 | 7 | 1 | 5 | 4 | 8 | 6 | 7 | 8 | 8 | 6 | | | | | | 6 | 5 | |
| | | | | | | | | | 5 | 5 | 4 | 9 | 8 | 9 | 9 | 9 | 9 | | | | | | 4 | 2 | |
| 126 | | | | | | | | | 1 | 4 | 2 | 9 | 8 | 8 | 9 | 9 | 8 | | | | | | | | |
| | | | | | | | | | 5 | 6 | 3 | 9 | 5 | 8 | 7 | 9 | 9 | 3 | | 3 | 4 | 4 | 9 | 9 | 8 |
| 127 | | | | | | | | | 1 | 6 | 1 | 9 | 4 | 6 | 7 | 9 | 9 | | | | | | 4 | 3 | 2 |
| | | | | | | | | | 5 | | | 8 | 6 | 8 | 9 | 9 | 7 | | | | | | | | |
| 128 | | | | | | | | | 1 | | | 8 | 5 | 7 | 8 | 9 | 7 | | | | | | | | |
| | | | | | | | | | 5 | | | 8 | 3 | 9 | 9 | 9 | 6 | | | | | | 4 | 4 | |
| 129 | | | | | | | 6 | | 1 | | | 4 | | 8 | 9 | 5 | 2 | | | | | | 4 | 3 | |
| | | | | | | | | | 5 | 4 | | 8 | 4 | 8 | 9 | 9 | 7 | | | | | | | | |
| 130 | | | | | | | | | 1 | | | 5 | 3 | 7 | 9 | 9 | 6 | | | | | | | | |
| | | | | | | | | | 5 | | | 8 | 3 | 9 | 9 | 9 | 6 | | | | | | | | |
| 131 | 4 | | 8 | 5 | 6 | 7 | 9 | 5 | 1 | | | 2 | | 8 | 9 | 8 | 5 | | | | | | | | |
| | | | | | | | | | 5 | | | 9 | 6 | 8 | 9 | 9 | 7 | | | 8 | 2 | 3 | 9 | 9 | 2 |
| 132 | 5 | 4 | 8 | 5 | 9 | 8 | 9 | 8 | 1 | | | 8 | 2 | 5 | 9 | 9 | 6 | | | 4 | | | 7 | 2 | |
| | | | | | | | | | 5 | 2 | | 9 | 5 | 9 | 9 | 9 | 7 | 5 | | 8 | | 9 | 9 | 9 | 2 |
| 133 | 7 | 6 | 8 | | 6 | 4 | 9 | 8 | 1 | | | 9 | 2 | 6 | 9 | 9 | 5 | 2 | | 4 | 2 | 8 | 8 | 5 | |
| | | | | | | | | | 5 | | 4 | 9 | 3 | 7 | 9 | 9 | 8 | | | 9 | 2 | 6 | 9 | 8 | 2 |
| 134 | | | | | | | | | 1 | | | 8 | | 5 | 8 | 9 | 5 | | | 8 | | 2 | 8 | 6 | |
| | | | | | | | | | 5 | | | | | 6 | 9 | 9 | 6 | | | | | | | | |
| | | | | | | | | | 1 | | | | | 6 | 9 | 8 | 4 | | | | | | | | |
| 135 | | | | | | 4 | 5 | | 5 | 5 | 4 | 9 | 4 | 8 | 9 | 9 | 8 | | | | | | 6 | 9 | |
| | | | | | | | | | 1 | 2 | 2 | 9 | 3 | 7 | 8 | 8 | 7 | | | | | | 4 | 7 | |

TABLE 3-continued

| Ex. No. | Dosage | | | | | | | | | | | | | | | | | | | | | |
|---|---|---|---|---|---|---|---|---|---|---|---|---|---|---|---|---|---|---|---|---|---|---|
| 136 | 5 | | | | 3 | 6 | 8 | | 5 | 6 | 4 | 8 | 6 | 9 | 9 | 9 | 7 | | | | 7 | 6 |
|  | 1 | | | | | | | | 2 | | | 8 | 5 | 7 | 8 | 7 | 7 | | | | 4 | 2 |
| 137 | 5 | | 4 | 5 | 4 | 7 | 6 | | 3 | 5 | | 9 | 6 | 8 | 9 | 9 | 6 | | | | 6 | 2 |
|  | 1 | | | | | | | | | 2 | | 8 | 5 | 7 | 8 | 9 | 5 | | | | 4 | |
| 138 | 5 | | | | 5 | 4 | 6 | | 4 | 3 | | 9 | 6 | 7 | 9 | 9 | 7 | | | | 8 | 8 |
|  | 1 | | | | | | | | 3 | 2 | | 8 | 5 | 7 | 8 | 8 | 6 | | | | 4 | 7 |
| 139 | 5 | | 4 | | 6 | 7 | 4 | | 4 | 3 | | 8 | 5 | 7 | 9 | 9 | 7 | | | | 6 | |
|  | 1 | | | | | | | | | 3 | | 8 | 5 | 4 | 8 | 8 | 5 | | | | 2 | |
| 140 | 5 | * | * | * | * | * | * | * | * | 3 | 4 | 8 | 5 | 6 | 8 | 9 | 5 | | | | 6 | 6 |
|  | 1 | | | | | | | | | 3 | 3 | 8 | 5 | 5 | 7 | 8 | 5 | | | | 5 | 2 |
| 141 | 5 | | | | 5 | 7 | | | | | | 9 | 7 | 9 | 9 | 9 | 7 | | | | 6 | 3 |
|  | 1 | | | | | | | | | | | 9 | 5 | 7 | 8 | 8 | 6 | | | | 4 | |
| 142 | 5 | 6 | | 7 | 7 | 9 | 9 | 9 | 6 | 3 | | 9 | 5 | 7 | 9 | 9 | 7 | | | | | |
|  | 1 | | | | | | | | | | | 7 | 2 | 6 | 8 | 8 | 6 | | | | | |
| 143 | 5 | | 6 | 4 | 6 | 8 | 6 | 5 | | | | 8 | 4 | 7 | 8 | 9 | 2 | | 4 | | 8 | 9 |
|  | 1 | | | | | | | | | | | 7 | | 6 | 8 | 8 | | | | | 1 | 4 |
| 144 | 5 | 7 | 3 | 8 | 7 | 4 | 9 | 9 | 8 | 6 | | 9 | 6 | 8 | 9 | 9 | 7 | 4 | 9 | 6 | 5 | 9 | 9 |
|  | 1 | | | | | | | | | | | 8 | 5 | 7 | 8 | 9 | 6 | 3 | 9 | 2 | | 8 | 8 |
| 145 | 5 | 4 | | 8 | 7 | 6 | 9 | 9 | 5 | 2 | | 9 | 6 | 8 | 9 | 9 | 5 | | 8 | 2 | 1 | 8 | 9 |
|  | 1 | | | | | | | | | | | 8 | 2 | 6 | 9 | 9 | 4 | | 6 | | | 2 | 2 |
| 146 | 5 | | | | | | | | 5 | | | 8 | 3 | 8 | 9 | 9 | 6 | | | | | |
|  | 1 | | | | | | | | 2 | | | 4 | | 8 | 9 | 9 | 5 | | | | | |
| 147 | 5 | | | | | | | | 1 | 3 | | 5 | 8 | 8 | 4 | 3 | 2 | | | | 4 | 3 |
|  | 1 | | | | | | | | | | | | 2 | 6 | 7 | | | | | | | |
| 148 | 5 | | | 1 | 3 | 2 | 8 | | | 2 | 7 | 3 | 5 | 9 | 8 | 2 | | | | | | |
|  | 1 | | | | | | | | | | | 4 | | 5 | 7 | 8 | | | | | | |
| 149 | 5 | 7 | 6 | 8 | 5 | 3 | 9 | 8 | 8 | 3 | | 9 | 4 | 6 | 9 | 9 | 8 | | 7 | 1 | 2 | 7 | 3 | 3 |
|  | 1 | | | | | | | | | | | 5 | 1 | 6 | 8 | 8 | 5 | | | | | 2 | 3 |
| 150 | 5 | 7 | 7 | 9 | 8 | 4 | 9 | 9 | 9 | | | 9 | 3 | 7 | 9 | 9 | 8 | 2 | 2 | 7 | 5 | 4 | 8 | 8 | 8 |
|  | 1 | | | | | | | | | | | 9 | 2 | 6 | 9 | 9 | 8 | | | 5 | | | 7 | 2 | 2 |
| 151 | 5 | | | | | | | | 4 | | | | 5 | 6 | | | | | | | | | |
|  | 1 | | | | | | | | 2 | | | | 2 | 2 | | | | | | | | | |
| 152 | 5 | * | * | * | * | * | * | * | * | 7 | | | 6 | 5 | | | | | | | | | |
|  | 1 | | | | | | | | | | | | 2 | 2 | | | | | | | | | |
| 153 | 5 | | | | | | | | | 1 | | | 4 | | | | | | | | | | |
|  | 1 | | | | | | | | | | | | 2 | | | | | | | | | | |
| 154 | 5 | | | | | | | | 4 | | 6 | | | 2 | | 2 | | | | | | | |
|  | 1 | | | | | | | | 2 | | | | | | | | | | | | | | |
| 156 | 5 | | | | | | | | 6 | | 7 | 4 | 5 | 6 | 7 | 4 | | | | | | | |
|  | 1 | | | | | | | | | | 5 | | 2 | | | | | | | | | | |
| 158 | 5 | | | | | | | | 4 | | | 2 | 4 | 8 | 4 | | | | | | | | |
|  | 1 | | | | | | | | | | | | | 2 | | | | | | | | | |
| 161 | 5 | | | | | | | | 2 | | 4 | 2 | 2 | 2 | 6 | 5 | 5 | | | | | | |
|  | 1 | | | | | | | | | | | | | | | 2 | | | | | | | |
| 162 | 5 | | | | | | | | | | 7 | | 4 | 5 | 3 | 4 | | | | | | | |
|  | 1 | | | | | | | | | | | | | 2 | | 2 | | | | | | | |
| 163 | 5 | | | | | | | | | | | | | 4 | 5 | | | | | | | | |
|  | 1 | | | | | | | | | | | | | 4 | 4 | | | | | | | | |
| 164 | 5 | | | | | | | | | | 4 | | 2 | 4 | 8 | 4 | | | | | | | |
|  | 1 | | | | | | | | | | | | | | 2 | | | | | | | | |
| 165 | 5 | | | | | | | | | | | | 4 | 2 | 6 | 3 | | | | | | | |
|  | 1 | | | | | | | | | | | | 1 | | 2 | | | | | | | | |
| 166 | 5 | | | | | | | | | | 6 | | | 4 | 3 | 2 | | | | | | | |
|  | 1 | | | | | | | | | | 2 | | | 2 | | | | | | | | | |
| 167 | 5 | | | | | | | | 2 | | 8 | | 2 | 3 | 4 | 4 | | | | | | | |
|  | 1 | | | | | | | | | | 2 | | | 2 | 2 | 2 | | | | | | | |
| 169 | 5 | | | | 2 | 4 | 2 | 1 | | | 5 | | | | 4 | | | | | | | | |
|  | 1 | | | | | | | | | | | | | | | | | | | | | | |
| 172 | 5 | | 3 | 3 | 5 | | | | | | | 6 | 2 | 4 | 5 | 6 | 5 | | | | | | |
|  | 1 | | | | | | | | | | | | | | 2 | 2 | 2 | | | | | | |
| 174 | 5 | | | | | | | | | | | | | 6 | 5 | | | | | | | | |
|  | 1 | | | | | | | | | | | | | 6 | 2 | | | | | | | | |

| | | Pre-Emergence | | | | | | | | | | | | | |
|---|---|---|---|---|---|---|---|---|---|---|---|---|---|---|---|
| Ex. No. | Dosage | TRZWA | HORVW | ZEAMX | HELAN | ALOMY | SETVI | GALAP | STEME | VERPE | CHEAL | MATIN | IPOHE | ABUTH | AMBEL | AMARE |
| 193 | 0.8 | | | | | | | | | | 1 | | | | | |
|  | 0.4 | | | | | | | | | | 1 | | | | | |
| 194 | 0.8 | | | | 1 | | | | | 1 | 1 | | | | | |
|  | 0.4 | | | | 1 | | | | | | 1 | | | | | |
| 195 | 0.8 | | | | | | | | | | 2 | | | | 2 | |
|  | 0.4 | | | | | | | | | | 2 | | | | 2 | |
| 196 | 0.8 | | | | | 2 | | 4 | 8 | 5 | 5 | | | | | 4 |
|  | 0.4 | | | | | | | 1 | 6 | 5 | 1 | | | | | 2 |

TABLE 3-continued

| Ex. No. | Dosage kg/ha | | | | | | | | | | | | | | | | |
|---|---|---|---|---|---|---|---|---|---|---|---|---|---|---|---|---|---|
| 197 | 0.8 | | | | | | 6 | 4 | 2 | 2 | | | 1 | 2 |
| | 0.4 | | | | | | | | 1 | | | | 1 | 1 |
| 198 | 0.8 | | 1 | 1 | | | 9 | 6 | 8 | 9 | 1 | 8 | 7 | 6 |
| | 0.4 | | | | | | 8 | 5 | 8 | 8 | | 3 | 4 | 4 |
| 199 | 0.8 | | 1 | | | | 1 | | 2 | 5 | 1 | | 1 | 2 |
| | 0.4 | | | | | | | | 2 | | | | | 1 |
| 200 | 0.8 | | 1 | 2 | | | 7 | 7 | 8 | 5 | | 3 | 2 | 7 |
| | 0.4 | | | 1 | | | | 6 | 2 | | | | 1 | 3 |
| 201 | 0.8 | | 1 | | | | 5 | 4 | 7 | 7 | | | | 5 |
| | 0.4 | | | | | | 2 | | 7 | | | | | 3 |
| 202 | 0.8 | | | | | 2 | 8 | 9 | 4 | 6 | | | 2 | 8 |
| | 0.4 | | | | | | 5 | 3 | 4 | 3 | | | | 7 |
| 203 | 0.8 | | | 2 | | | 4 | 4 | 7 | 8 | | 1 | 2 | 6 |
| | 0.4 | | | | | | 3 | | 7 | 6 | | | 1 | 2 |
| 204 | 0.8 | | 2 | 4 | 3 | | 9 | 8 | 8 | 9 | 3 | 8 | 8 | 8 |
| | 0.4 | | 1 | 1 | 1 | | 8 | 7 | 8 | 9 | | 8 | 7 | 5 |

| | Soil drench 10 kg/ha | | | | | | | | Dosage | Foliar Spray | | | | | | | | Pre-emergence | | | | | | | |
|---|---|---|---|---|---|---|---|---|---|---|---|---|---|---|---|---|---|---|---|---|---|---|---|---|---|
| Ex. No. | Z | R | G | O | L | M | B | S | kg/ha | Z | R | G | O | L | M | B | S | Z | R | G | O | L | M | B | S |
| 206 | 0 | 0 | 3 | 2 | 2 | 9 | 7 | 4 | 5 | 0 | 0 | 7 | 0 | 3 | 8 | 8 | 3 | 0 | 0 | 0 | 0 | 0 | 5 | 4 | 2 |
| | | | | | | | | | 1 | 0 | 0 | 0 | 0 | 0 | 6 | 2 | 0 | 0 | 0 | 0 | 0 | 0 | 0 | 0 | 0 |
| 207 | 0 | 0 | 0 | 0 | 0 | 7 | 2 | 0 | 5 | 1 | 0 | 4 | 1 | 0 | 8 | 9 | 2 | 0 | 0 | 0 | 0 | 0 | 0 | 0 | 0 |
| | | | | | | | | | 1 | 0 | 0 | 0 | 0 | 0 | 7 | 3 | 1 | 0 | 0 | 0 | 0 | 0 | 0 | 0 | 0 |
| 217 | 3 | 0 | 7 | 7 | 9 | 9 | 9 | 1 | 5 | 3 | 3 | 9 | 3 | 8 | 9 | 9 | 4 | 1 | 0 | 0 | 0 | 0 | 5 | 8 | 0 |
| | | | | | | | | | 1 | 3 | 6 | 5 | 2 | 6 | 9 | 9 | 1 | 0 | 0 | 0 | 0 | 0 | 0 | 0 | 0 |
| 218 | 0 | 0 | 0 | 0 | 0 | 6 | 5 | 1 | 5 | 3 | 1 | 5 | 0 | 3 | 8 | 8 | 2 | 0 | 0 | 0 | 0 | 0 | 0 | 0 | 0 |
| | | | | | | | | | 1 | 0 | 0 | 0 | 0 | 3 | 8 | 6 | 0 | 0 | 0 | 0 | 0 | 0 | 0 | 0 | 0 |
| 219 | 2 | 0 | 5 | 2 | 5 | 8 | 9 | 2 | 5 | 4 | 0 | 7 | 5 | 8 | 8 | 9 | 6 | 4 | 0 | 0 | 0 | 0 | 9 | 8 | 0 |
| | | | | | | | | | 1 | 0 | 0 | 0 | 2 | 4 | 7 | 8 | 5 | 0 | 0 | 0 | 0 | 0 | 5 | 4 | 0 |
| 229 | 0 | 0 | 0 | 0 | 0 | 8 | 3 | 0 | 5 | 0 | 0 | 7 | 0 | 5 | 7 | 7 | 0 | 0 | 0 | 0 | 0 | 0 | 0 | 0 | 0 |
| | | | | | | | | | 1 | 0 | 0 | 0 | 6 | 2 | 6 | 5 | 0 | 0 | 0 | 0 | 0 | 0 | 0 | 0 | 0 |
| 230 | 0 | 0 | 4 | 5 | 6 | 7 | 5 | 0 | 5 | 4 | 0 | 5 | 2 | 6 | 7 | 8 | 2 | 0 | 0 | 5 | 0 | 0 | 6 | 8 | 0 |
| | | | | | | | | | 1 | 2 | 0 | 2 | 0 | 2 | 5 | 2 | 0 | 0 | 0 | 2 | 0 | 0 | 4 | 5 | 0 |
| 231 | 2 | 1 | 5 | 7 | 5 | 9 | 9 | 4 | 5 | 5 | 0 | 6 | 2 | 8 | 9 | 9 | 5 | 0 | 0 | 0 | 0 | 0 | 5 | 7 | 0 |
| | | | | | | | | | 1 | 4 | 0 | 5 | 0 | 5 | 8 | 8 | 4 | 0 | 0 | 0 | 0 | 0 | 2 | 5 | 0 |
| 232 | 2 | 6 | 6 | 2 | 4 | 8 | 8 | 7 | 5 | 1 | 1 | 9 | 5 | 4 | 8 | 8 | 8 | 0 | 0 | 2 | 0 | 2 | 8 | 4 | 2 |
| | | | | | | | | | 1 | 1 | 0 | 6 | 1 | 4 | 8 | 6 | 6 | 0 | 0 | 0 | 0 | 0 | 0 | 2 | 0 |
| 233 | 6 | 2 | 8 | 8 | 4 | 9 | 9 | 6 | 5 | 5 | 0 | 9 | 5 | 8 | 9 | 9 | 8 | 2 | 0 | 6 | 0 | 5 | 9 | 7 | 0 |
| | | | | | | | | | 1 | 4 | 0 | 8 | 4 | 5 | 8 | 9 | 5 | 0 | 0 | 2 | 0 | 2 | 5 | 4 | 0 |
| 234 | 4 | 0 | 6 | 5 | 5 | 8 | 8 | 4 | 5 | 4 | 0 | 9 | 0 | 6 | 8 | 9 | 5 | 0 | 0 | 0 | 0 | 0 | 0 | 0 | 0 |
| | | | | | | | | | 1 | 2 | 0 | 7 | 0 | 4 | 7 | 8 | 2 | 0 | 0 | 0 | 0 | 0 | 0 | 0 | 0 |
| 235 | 2 | 0 | 5 | 4 | 5 | 8 | 4 | 1 | 5 | 5 | 0 | 6 | 2 | 4 | 9 | 6 | 5 | 0 | 0 | 0 | 0 | 0 | 7 | 5 | 0 |
| | | | | | | | | | 1 | 4 | 0 | 5 | 0 | 2 | 7 | 5 | 4 | 0 | 0 | 0 | 0 | 0 | 5 | 2 | 0 |
| 236 | 0 | 0 | 2 | 1 | 3 | 5 | 5 | 0 | 5 | 0 | 0 | 0 | 0 | 0 | 8 | 6 | 2 | 0 | 0 | 0 | 0 | 0 | 7 | 2 | 0 |
| | | | | | | | | | 1 | 0 | 0 | 0 | 0 | 0 | 8 | 6 | 2 | 0 | 0 | 0 | 0 | 0 | 1 | 0 | 0 |

I claim:

1. A method of combating undesired plant growth at a locus comprising application to the locus of a herbicidal composition which composition comprises an agronomically acceptable carrier, and at least one compound of formula I

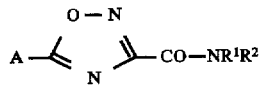

(I)

wherein

A represents an optionally substituted alkyl, alkenyl, alkynyl or cycloalkyl group;

$R^1$ represents a hydrogen atom or an alkyl group;

$R^2$ represents an optionally substituted aralkyl or heteroaralkyl group; wherein the optional substituents for alkyl, alkenyl, alkynyl, and cycloalkyl, and alkyl portions of aralkyl or heteroaralkyl groups are independently selected from the group consisting of halogen, nitro, cyano, hydroxyl, $C_{1-4}$ alkoxy, $C_{1-4}$ haloalkoxy, $C_{1-4}$ alkoxycarbonyl, amino, alkyl- and phenyl-sulphinyl, -sulphenyl and -sulphonyl, and $C_{1-4}$ alkylamino groups, and optional substituents for aryl portions of aralkyl and heteroaralkyl groups are independently selected from the group consisting of halogen, amino, nitro, cyano, hydroxyl, $C_{1-4}$ alkyl, $C_{1-4}$ haloalkyl, and $C_{1-4}$ alkoxy groups.

2. A method according to claim 1, wherein in said at least one compound of formula I A represents a branched alkyl, alkenyl, or alkynyl group containing up to 6 carbon atoms.

3. A method according to claim 1, wherein in said at least one compound of formula I A represents a branched alkyl group having 3 to 6 carbon atoms.

4. A method according to claim 1, wherein in said at least one compound of formula I $R^1$ represents a hydrogen atom; and $R^2$ represents optionally substituted heteroaralkyl.

5. A method according to claim 4 wherein in said at least one compound of formula I $R^1$ represents a hydrogen atom; and $R^2$ represents a group of formula

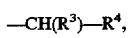

in which $R^3$ represents hydrogen or a $C_{1-4}$ alkyl group; and $R^4$ represents a pyridyl, furyl or thienyl group.

6. A method according to claim 5, wherein in said at least one compound of formula I A represents a branched alkyl group having 3 to 6 carbon atoms;

$R^1$ represents a hydrogen atom; and $R^2$ represents a group of formula

—CH($R^3$)—$R^4$, in which $R^3$ represents hydrogen or a $C_{1-4}$ alkyl group; and $R^4$ represents a pyridyl, furyl or thienyl group.

7. A method according to claim 5 wherein said at least one compound of formula I is optically active and $R^1$ represents a hydrogen atom; and $R^2$ represents a chiral group having (S)-configuration of formula

—CH($R^3$)—$R^4$, in which $R^3$ represents a $C_{1-4}$ alkyl group; and $R^4$ represents a pyridyl, furyl or thienyl group.

* * * * *

UNITED STATES PATENT AND TRADEMARK OFFICE
CERTIFICATE OF CORRECTION

PATENT NO. : 5,707,935
DATED : January 13, 1998
INVENTOR(S) : W. Buck

It is certified that error appears in the above-identified patent and that said Letters Patent is hereby corrected as shown below:

Title page, item (73) Assignee: should read --Shell Research Limited--

Signed and Sealed this

Twenty-second Day of August, 2000

Attest:

Q. TODD DICKINSON

*Attesting Officer*            *Director of Patents and Trademarks*